(12) United States Patent
Dornan et al.

(10) Patent No.: US 7,785,815 B2
(45) Date of Patent: Aug. 31, 2010

(54) COP1 MOLECULES AND USES THEREOF

(75) Inventors: David Dornan, Burlingame, CA (US);
Dorothy French, San Carlos, CA (US);
Vishva Dixit, Los Altos, CA (US)

(73) Assignee: Genentech, Inc., South San Francisco, CA (US)

( * ) Notice: Subject to any disclaimer, the term of this patent is extended or adjusted under 35 U.S.C. 154(b) by 98 days.

(21) Appl. No.: 11/786,399

(22) Filed: Apr. 10, 2007

(65) Prior Publication Data

US 2008/0009458 A1 Jan. 10, 2008

Related U.S. Application Data

(63) Continuation of application No. PCT/US2004/034174, filed on Oct. 14, 2004.

(51) Int. Cl.
*G01N 33/53* (2006.01)
*C12Q 1/68* (2006.01)

(52) U.S. Cl. .......................... 435/7.23; 435/6; 436/536; 436/518

(58) Field of Classification Search .................. None
See application file for complete search history.

(56) References Cited

FOREIGN PATENT DOCUMENTS

| WO | WO 1992/13970 A | 8/1992 |
| WO | WO 2004/013632 A1 | 2/2004 |
| WO | WO 2004/025251 A2 | 3/2004 |

OTHER PUBLICATIONS

Allan et al, "p53-dependent apoptosis or growth arrest induced by different forms of radiation in U2OS cells: p21WAF1/CIP1 repression in UV induced apoptosis" Oncogene. 23;18(39):5403-12 1999.
Altschul, S.F. 1991. Journal of Molecular Biology, 219: 555-665.
Ang et al, "Molecular interaction between COP1 and HY5 defines a regulatory switch for light control of *Arabidopsis* development," Mol Cell 1, 213-22 (1998).
Barak et al, "mdm2 expression is induced by wild type p53 activity," Embo J 1993, 12:461-468.
Beroud et al, "The UMD-p53 database: new mutations and analysis tools," Hum Mutat 2003, 21:176-181.
Bianchi et al, "Characterization of human constitutive photomorphogenesis protein 1, a RING finger ubiquitin ligase that interacts with Jun transcription factors and modulates their transcriptional activity," J Biol Chem 2003, 278:19682-19690.
Cao et al, "Abrogation of wild-type p53-mediated transactivation is insufficient for mutant p53-induced immortalization of normal human mammary epithelial cells," Cancer Res 1997, 57:5584-5589.
Corcoran et al, "The p53 paddy wagon: COP1, Pirh2 and MDM2 are found resisting apoptosis and growth arrest," Cancer Biology & Therapy vol. 3, No. 8, pp. 721-725 (2004).
Craig et al, "Novel phosphorylation sites of human tumour suppressor protein p53 at Ser20 and Thr18 that disrupt the binding of mdm2 (mouse double minute 2) protein are modified in human cancers," Biochem J 1999, 342 ( Pt 1):133-141.

Dayhoff, M.O., "A model of evolutionary change in proteins", Atlas of Protein Sequence and Structure, 5(3) 345-352 1978.
Donehower et al, "Mice deficient for p53 are developmentally normal but susceptible to spontaneous tumours," Nature 1992, 356:215-221.
Dornan et al, "COP1, the negative regulator of p53, is overexpressed in breast and ovarian adenocrcinomas", Cancer Research, vol. 64, No. 20, pp. 7226-7230 (2004).
Dornan et al, "DNA-dependent acetylation of p53 by the transcription coactivator p300," J Biol Chem 278, 13431-41 (2003).
Dornan et al, "Inhibition of p53-dependent transcription by BOX-I phospho-peptide mimetics that bind to p300," EMBO Rep 2, 139-44 (2001).
Dornan et al, "The ubiquitin ligase COP1 is a cirtical negative regulator of p53", Nature vol. 429, No. 6987 pp. 86-92.
Dornan et al, "ATM engages auto-degredation of the E3 ubiquitin ligase COP1 to activate p53 in response to DNA damage", 97th AACR Annual Meeting, Apr. 1-5, 2006 Washington D.C.
Eisenberg et al, J. Mol. Bio. 179:125-142, 184.
Frantz et al, "Detection of novel gene expression in paraffin-embedded tissues by isotopic in situ hybridization in tissue microarrays," J Pathol 195, 87-96 (2001).
Hardtke et al, "The cell biology of the COP/DET/FUS proteins. Regulating proteolysis in photomorphogenesis and beyond?", Plant Physiol 124, 1548-57 (2000).
Haupt et al, "Mdm2 promotes the rapid degradation of p53," Nature 1997, 387:296-299.
Henikoff et al, "Amino acid substitution matrices from protein blocks." Proc. Natl. Acad. Sci. USA. 89(biochemistry): 10915-10919 (1992).
Henikoff et al, "Performance Evaluation of Amino Acid Substitution Matrices." Proteins: Structure, Function, and Genetics. 17: 49-61 (1993).
Ho et al, "Transcriptional repression mediated by the p53 tumour suppressor," Cell Death Differ 2003, 10:404-408.
Honda et al, "Oncoprotein MDM2 is a ubiquitin ligase E3 for tumor suppressor p53," FEBS Lett 1997, 420:25-27.
Hupp et al, "Strategies for manipulating the p53 pathway in the treatment of human cancer," Biochem J 2000, 352 Pt 1:1-17.
Jin et al, "The p53 functional circuit," J Cell Sci 114, 4139-40 (2001).
Johnson et al, "A Structural Basis of Sequence Comparisons: An evaluation of scoring methodologies," Journal of Molecular Biology. 233: 716-738 (1993).
Juven et al, "Wild type p53 can mediate sequence-specific transactivation of an internal promoter within the mdm2 gene," Oncogene 1993, 8:3411-3416.
Karlin et al, "Methods for assessing the statistical significance of molecular sequence features by using general scoring schemes" Proc. Natl. Acad. Sci. USA. 87: 2264-2268 (1990).
Kmet et al, "A review of p53 expression and mutation in human benign, low malignant potential, and invasive epithelial ovarian tumors," Cancer 97:389-404, 2003.

(Continued)

*Primary Examiner*—Misook Yu
(74) *Attorney, Agent, or Firm*—Elizabeth M. Barnes; Jeffrey P. Bernhardt; Ginger R. Dreger

(57) ABSTRACT

The invention provides diagnostic, prognostic, and therapeutic uses for detecting COP1 overexpression in a variety of cancers. The methods and uses can further include detecting p53 expression. The invention also provides reagents and kits for use in screening for test compounds that interfere with COP1 and p53 binding.

19 Claims, 11 Drawing Sheets

OTHER PUBLICATIONS

Kubbutat et al, "Regulation of p53 stability by Mdm2," Nature 1997, 387:299-303.

Leng et al, "Pirh2, a p53-induced ubiquitin-protein ligase, promotes p53 degradation," Cell 2003, 112:779-791.

Ma et al, "Genomic evidence for COP1 as a repressor of light-regulated gene expression and development in *Arabidopsis*," Plant Cell 14, 2383-98 (2002).

Ma et al, "Light control of *Arabidopsis* development entails coordinated regulation of genome expression and cellular pathways," Plant Cell 13, 2589-607 (2001).

Neff et al, "Light: an indicator of time and place," Genes Dev 14, 257-71 (2000).

Oren et al, "Decision making by p53: life, death and cancer," Cell Death Differ 10, 431-42 (2003).

Qian et al, "Groups of p53 target genes involved in specific p53 downstream effects cluster into different classes of DNA binding sites," Oncogene 21, 7901-11 (2002).

Reyes, "PML and COP1—two proteins with much in common," Trends in Biochemical Sciences, vol. 26, No. 1, pp. 18-20 (2001).

Ross et al, "Prostate stem cell antigen as therapy target: tissue expression and in vivo efficacy of an immunoconjugate," Cancer Res 62, 2546-53 (2002).

Schuijer et al, "TP53 and ovarian cancer," Hum Mutat 21, 285-91 (2003).

Seo et al, "LAF1 ubiquitination by COP1 controls photomorphogenesis and is stimulated by SPA1," Nature 424, 995-9 (2003).

Shimizu et al, "Intrasteric regulation of MDM2," Trends Biochem Sci 28, 346-9 (2003).

Shimizu et al, "The conformationally flexible S9-S10 linker region in the core domain of p53 contains a novel MDM2 binding site whose mutation increases ubiquitination of p53 in vivo," J. Biol. Chem. 277, 28446-28458 (2002).

Soussi et al, "p53 Website and analysis of p53 gene mutations in human cancer: forging a link between epidemiology and carcinogenesis," Human Mutation 15: 105-113, 2000.

Soussi et al, "Significance of TP53 mutations in human cancer: a critical analysis of mutations at CpG dinucleotides," Hum Mutat 2003, 21:192-200.

States et al, "Improved Sensitivity of Nucleic Acid Database Search Using Application-Specific Scoring Matrices" Methods: A companion to Methods in Enzymology 3(1): 66-77 (1991).

Swinney et al, "A small molecule ubiquitination inhibitor blocks NF-kB dependent cytokine expresion in cells and rats," J. Biol. Chem. 277: 23573-23581, 2002.

Varadan et al, "Solution conformation of Lys63-linked di-ubiquitin chain provides clues to functional diversity of polyubiquitin signaling," J Biol Chem 2004, 279:7055-7063.

Vogelstein et al, "Surfing the p53 network", Nature 2000, 408:307-310.

Wang et al "Evidence for functional conservation of a mammalian homologue of the light-responsive plant protein COP1," Current Biology 9:711-714, 1999.

Weinberg R, "Tumor suppressor gene", Science 254:1138-1145, 1991.

Wertz et al, "Human De-etiolated-1 regulates c-Jun by assembling a CUL4A ubiquitin ligase," Science 303, 1371-1374 (2004).

Xu et al, "p53 responsive genes and the potential for cancer diagnostics and therapeutics development," Biotechnology Annual Review 7:131-164, 2001.

Yi et al, "An initial biochemical and cell biological characterization of the mammalian homologue of a central plant developmental switch, COP1," BMC Cell Biol 3, 30 (2002).

International Search Report and Written Opinion of the International Searching Authority for PCT/US2004/034174 dated Sep. 27, 2005.

Dornan, D. et al., "COP1, the Negative Regulator of p53, Is Overexpressed in Breast and Ovarian Adenocarcinomas", Cancer Research, vol. 64, pp. 7226-7230, 2004.

COP1 MOLECULES AND USES THEREOF

CROSS-REFERENCE TO RELATED APPLICATIONS

This application is a continuation under 37 C.F.R. 1.53(b) of International Patent Application PCT/US2004/034174 filed on Oct. 14, 2004, the contents of which are incorporated herein by reference.

FIELD OF THE INVENTION

The invention is in the field of cancer diagnostics and therapeutics.

BACKGROUND OF THE INVENTION

The role of p53 as a classical tumour suppressor has been well established.[1] Biochemically, p53 functions as a stress-activated sequence-specific transcription factor that activates transcription from promoters that harbour a p53 consensus-binding site.[2] In addition, p53 also functions as a potent repressor of transcription, thereby adding a further layer of gene regulation.[3] As such, it protects cells from a variety of stress signals such as DNA damage, nucleotide depletion, and oncogene activation to name a few, by activating the transcription of a cadre of genes involved in cell cycle arrest, apoptosis and DNA repair in addition to repressing genes involved in angiogenesis, anti-apoptosis, and cell cycle progression. The physiological consequence of p53 activation essentially leads to growth arrest or apoptosis, thereby preventing cells from replicating a genetically compromised genome.

p53 is a potent tumour suppressor protein[26,27] that is negatively regulated or mutated in some, if not all, cancers. The high frequency of alternations in the p53 gene, or deregulated components of the p53 pathway, in human malignancies underscores the importance of p53 integrity to prevent carcinogenesis. This is further substantiated with the observations from the p53 knockout mice that develop spontaneous tumors by 6 months of age.[4] The actual frequency of p53 gene alterations in cancers is estimated to be 20-80%. The wide variation may be attributable to the tissue of tumor origin, detection methods, and/or the regions of the gene that are analysed. For example, in breast tumours the estimated frequency of gene alteration is about 20%, whereas this frequency dramatically increases to >70% in cases of small cell lung carcinomas.[5,6] Ovarian tumors generally have a wild type p53 gene[28].

p53 is rapidly turned over in unstressed cells by a proteasome-dependent pathway by substrate recognition for E3 ligases such as Pirh2[7] and MDM2,[8-10] which transfer ubiquitin from an E2 enzyme, such as UbCH5b, to a substrate on multiple lysine residues, or upon substrate-conjugated ubiquitin to generate a polyubiquitin chain. Once the K48-linked polyubiquitin chain length reaches 4 or more, the substrate can then be recognized by components of the proteasome such as hRad23a[11], targeting the substrate for degradation. Thus, MDM2[25] and Pirh2[7] are negative regulators of p53. Pirh2 and MDM2 are p53-inducible genes[7,12,13] thereby creating a negative feedback loop that may be employed to turn off the p53 response and allowing cell cycle progression.

*Arabidopsis thaliana* COP1 is a RING finger-containing protein that functions to repress plant photomorphogenesis. AtCOP1 controls seedling development by negatively regulating light-mediated gene expression[14] and microarray analysis indicates that AtCOP1 regulates most, if not all, genes that are light-responsive[15,16]. This can be exemplified by loss-of-function mutants of the COP/DET/FUS proteins that display a phenotype that is representative of light-grown plants in darkness 7. Mechanistically, this has been attributed to AtCOP1's ability to repress positive regulators of light-mediated development such as LAF1[18] and HY5[19]. COP1 has inherent E3-ligase activity in vitro[29,30] and can utilise LAF1 as a substrate. While COP1 is a critical light-mediated development switch in plants, its role in mammalian cells is less well established[20].

SUMMARY OF THE INVENTION

The present invention relates to a method for diagnosing a cancer in a subject, the method comprising detecting COP1 levels or activity in the cancer in the subject. In a further embodiment, the diagnosis method involves detecting the p53 levels or activity in the cancer of the subject. In one embodiment, the p53 molecule detected is a wild-type p53 molecule. In another embodiment, the p53 molecule is a human p53 molecule. In another embodiment the p53 molecule is detected using an antibody that specifically binds p53. In a further embodiment of the diagnosis method, the nucleic acid sequence of the p53 in the cancer is sequenced. In another embodiment, the p53 molecule is detected by using p53 activity assays selected from the group consisting of at least one of inhibition of p53-dependent transactivation, inhibition of p53-induced apoptosis, and reduction of p21 mRNA levels.

According to another embodiment, the diagnosis method comprises the step of detecting a p21 molecule in said sample. According to another embodiment, the subject being diagnosed is a human. According to yet another embodiment, the cancer being diagnosed is selected from the group consisting of at least one of breast cancer, ovarian cancer, colon cancer, lung cancer, and transitional cell cancer. According to yet another embodiment, the cancer being diagnosed is selected from the group consisting of serous adenocarcinoma, endometrioid adenocarcinoma, clear cell adenocarcinoma, and mucinous adenocarcinoma.

The present invention relates to a method for monitoring the efficacy or assessing the prognosis of a cancer therapy in a subject, the method comprising detecting a COP1 molecule in a sample from the subject, wherein a reduction in overexpression of said COP1 molecule relative to a control indicates that the cancer therapy is efficacious. In one embodiment, the method further comprises detecting a p53 molecule in said sample. In yet another embodiment, the p53 molecule being detected is a wild type p53. In another embodiment, the p53 molecule is detected by observing p53 activity selected from the group consisting of at least one of inhibition of p53-dependent transactivation, inhibition of p53-induced apoptosis, and reduction of p21 mRNA levels. In one embodiment, the cancer therapy being evaluated is for the treatment of a cancer that is selected from the group consisting of at least one of breast cancer, ovarian cancer, colon cancer, lung cancer, and transitional cell cancer. In one embodiment, the cancer therapy being evaluated is for the treatment of a cancer that is selected from at least one of a group consisting of serous adenocarcinoma, endometrioid adenocarcinoma, clear cell adenocarcinoma, and mucinous adenocarcinoma.

The present invention relates to methods of treating a cancer in a subject diagnosed with or at risk for a cancer, comprising: administering to the subject a therapeutically effective amount of a first compound that inhibits expression of COP1. In one embodiment, the method further comprises administering to the subject a therapeutically effective amount of a second compound that inhibits expression of MDM2 or Pirh2. In another embodiment, the first or second compound sensitizes the cancer to a cancer therapy. In yet another embodiment, the first or second compound is selected from at least one of the group consisting of antisense oligonucleotides, triple-strand forming oligonucleotides, and siRNA molecules. The method can further comprise the administration of one or more other therapeutic agents that may be useful during the course of cancer therapy, before, during or after the administration of the first and/or second compounds. In one embodiment, the cancer to be treated expresses a wild type p53. In another embodiment, the cancer to be treated overexpresses COP1 compared to a control. In another embodiment, the cancer to be treated expresses reduced p53 level or activity reduced compared to a control. In yet another embodiment, the cancer to be treated expresses reduced p21 expression levels compared to a control.

The present invention relates to a method of screening for a test compound that interferes with the binding of a COP1 molecule to a p53 molecule. In one embodiment, the test compound may further inhibit COP1 ligase activity. In another embodiment, the method further comprises determining whether said test compound modulates a COP1 activity. In one embodiment, the COP1 activity is selected from at least one of the group consisting of degradation of p53, ubiquitination of p53, inhibition of p53-dependent transactivation, inhibition of p53 induced apoptosis, and reduction of p21 mRNA levels. In one embodiment, the COP1 is human COP1 molecule. In another embodiment, the p53 is a human p53 molecule. In one embodiment, the screening method is an assay that measures disruption or inhibition of binding of COP1/p53. In another embodiment, the screening method is a reporter gene assay. In a further embodiment, the screening method involves the further step of detecting COP1 activity, wherein the activity is selected from at least one of the group consisting of degradation of p53, ubiquitination of p53, inhibition of p53-dependent transactivation, inhibition of p53 induced apoptosis, and reduction of p21 mRNA levels.

The present invention relates to a method for screening for compounds that inhibit the activity of p53 comprising the step of treating a mammalian cell with a test compound that binds to COP1 and detecting p53 in the treated cell. In one embodiment, the detecting step comprises measuring at least one of the group consisting of the degradation of p53, the ubiquitination of p53, the inhibition of p53 transactivation, the inhibition of p53 induced apoptosis, and the reduction of p21 mRNA levels. In one embodiment, the mammalian cell has been engineered to express COP1. In one embodiment, the mammalian cell has been engineered to express p53.

The present invention relates to the use of a compound that inhibits expression of a COP1 molecule or inhibits COP1 ligase activity for the preparation of a medicament for treating a cancer in a subject diagnosed with or at risk for a cancer. According to one embodiment, the compound is an RNAi that targets COP1. According to another embodiment, the medicament includes a compound that inhibits expression of MDM2 or Pirh2 or a label for the medicament provides information relating to administering a compound that inhibits expression of MDM2 or Pirh2 with the COP1-inhibiting compound. According to another embodiment, the medicament further comprises a compound that inhibits the expression or activity of a MDM2 molecule and/or can be accompanied with instructions for administering the MDM2 inhibitor. According to another embodiment, the medicament further comprises a compound that inhibits the expression or activity of Pirh2 and/or can be accompanied with instructions for administering the Pirh2 inhibitor.

The present invention relates to methods for inhibiting the activity of p53 in the mammalian cell comprising the step of overexpressing COP1 in a cell and detecting the p53 in the cell that is overexpressing COP1. The present invention also relates to mammalian cells comprising a recombinant nucleic acid molecule encoding a p53 molecule and a recombinant nucleic acid molecule encoding a mammalian COP1 molecule. The present invention also relates to mammalian cells engineered to have non-coding sequences (for example, promoter/enhancer sequences or antisense sequences) that increase or decrease expression of a p53 molecule in combination with non-coding sequences that increase or decrease COP1 molecule expression or with a molecule encoding a COP1 molecule. The present invention also relates to mammalian cells engineered to have non-coding sequences (for example, promoter/enhancer sequences or antisense sequences) that increase or decrease expression of a COP1 molecule in combination with non-coding sequences that increase or decrease p53 molecule expression or with a molecule encoding a p53 molecule. The present invention also relates to mammalian cells engineered to have coding sequences for p53 altered genomically so that p53 is not expressed or expressed as mutant in combination with engineering the cell to alter COP1 molecule expression or activity. The present invention also relates to mammalian cells engineered to have coding sequences for COP1 altered genomically so that COP1 is not expressed or expressed as mutant in combination with engineering the cell to alter p53 molecule expression or activity.

The present invention provides mammalian cells engineered to have reduced COP1 activity and reduced MDM2 activity, optionally further engineered to alter p53 expression or activity. The present invention provides mammalian cells engineered to have reduced COP1 activity and reduced Pirh2 activity, optionally further engineered to alter p53 expression or activity. The present invention provides mammalian cells engineered to have reduced COP1 activity, reduced MDM2 activity and reduced Pirh2 activity, optionally further engineered to have altered p53 expression or activity. The present invention provides mammalian cells engineered to have reduced MDM2 activity, reduced Pirh2 activity and increased COP1 activity. The present invention provides mammalian cells engineered to have reduced COP1 activity. The present invention provides mammalian cells engineered to have reduced p53 activity and increased or normal COP1 activity. In one embodiment, the activity is reduced by the method of RNAi that targets the p53 or COP1 molecule.

The present invention provides a cell comprising a first nucleic acid molecule comprising a sequence specific DNA binding domain operably linked to a nucleic acid molecule encoding a COP1 polypeptide, a second nucleic acid molecule comprising a transactivation domain operably linked to a nucleic acid molecule encoding a p53 polypeptide, and a third nucleic acid molecule comprising a reporter gene operably linked to a sequence capable of being recognized by said sequence specific DNA binding domain. The present invention also provides a cell comprising a first nucleic acid molecule comprising a sequence specific DNA binding domain operably linked to a nucleic acid molecule encoding a p53 polypeptide, a second nucleic acid molecule comprising a transactivation domain operably linked to a nucleic acid molecule encoding a COP1 polypeptide, and a third nucleic acid molecule comprising a reporter gene operably linked to a sequence capable of being recognized by said sequence specific DNA binding domain.

The present invention also provides assays comprising the use of a recombinant COP1 molecule in combination with the use of a recombinant p53 molecule, e.g., in vitro ubiquitin assays, COP1/p53 binding assays, COP1 ligase assays and p53 activity assays.

The present invention provides kits comprising a reagent for detecting COP1 molecules in a sample and a package insert containing instructions for detecting COP1 molecules in a sample comprising cancer cells. In one embodiment, the cancer cells are wild-type p53-expressing cancer cells. In another embodiment, the cancer cell is selected from the group consisting of at least one of breast cancer cell, ovarian cancer cell, colon cancer cell, lung cancer cell, and transitional cell cancer cell. In another embodiment, the cancer is selected from the group consisting of at least one of serous adenocarcinoma, endometrioid adenocarcinoma, clear cell adenocarcinoma, and mucinous adenocarcinoma. In one embodiment, the kit further comprises a reagent for detecting p53 molecules in a sample.

The present invention provides pharmaceutical compositions comprising a compound that that inhibits expression of COP1 together with a pharmaceutically acceptable carrier. In one embodiment, the pharmaceutical composition further comprises a compound that inhibits expression of MDM2 or Pirh2. In one embodiment, compound is selected from at least one of the group consisting of antisense oligonucleotides, triple-strand forming oligonucleotides, and siRNA molecules.

In one embodiment of the compositions and methods of this invention, the COP1 molecule comprises at least a portion of a human COP1, or variant thereof, that binds p53. In one embodiment of the methods of this invention, the p53 molecule comprises at least a portion of human p53, or variant thereof, that binds COP1. In another embodiment of the compositions and methods of this invention, the COP1 molecule comprises at least a portion of a human COP1, or variant thereof, that binds p53 in combination with the portion of COP1 having ligase activity. In one embodiment, the inhibitors of COP1, p53, p21, MDM2 and Pirh2 of this invention inhibit by binding to COP1, p53, p21, MDM2 and Pirh2 or to genes encoding COP1, p53, p21, MDM2 and Pirh2, including untranslated regions of those genes.

DETAILED DESCRIPTION OF THE INVENTION

Figure 1:
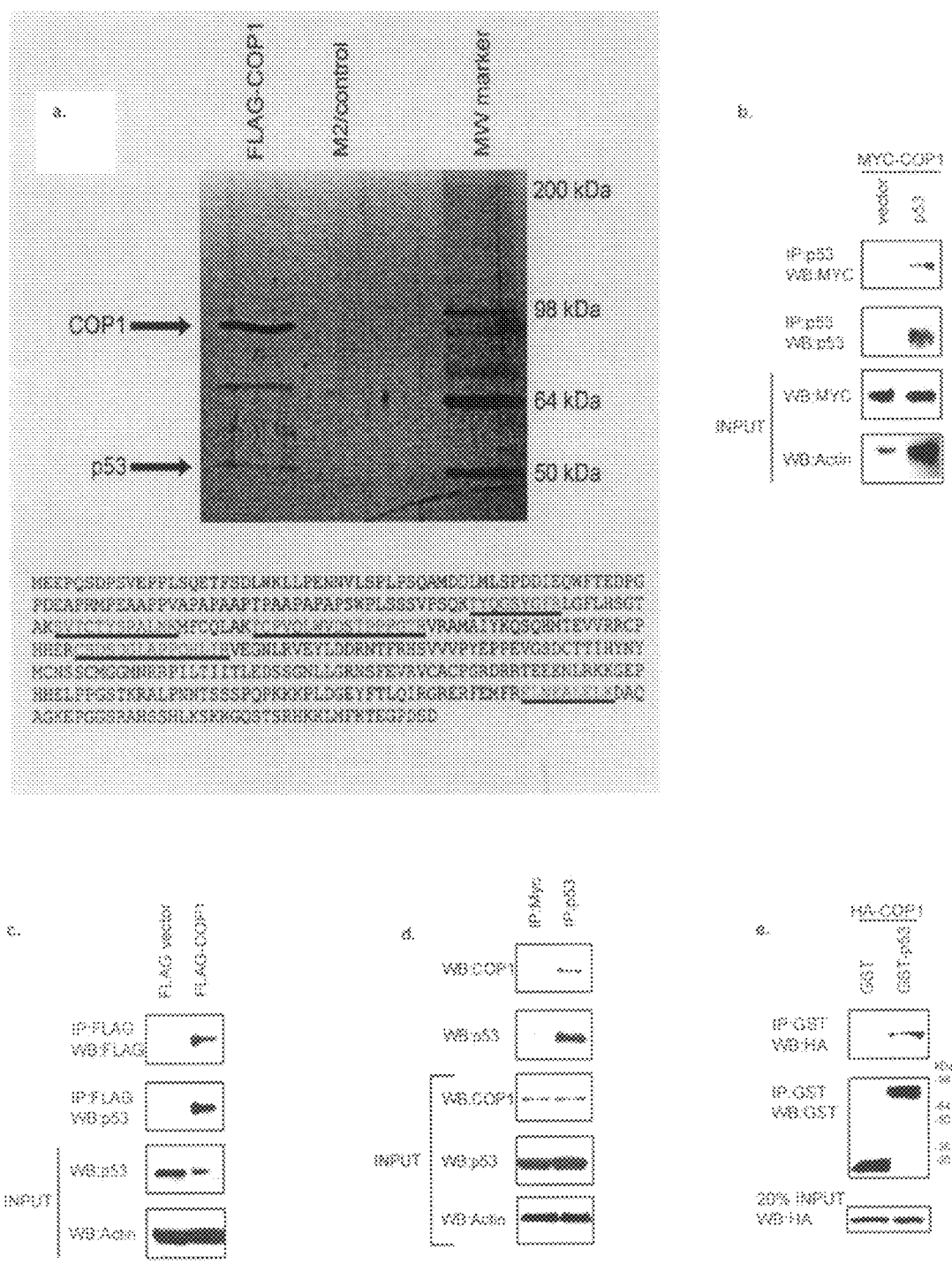
FIGS. 1A-E. COP1 and its interaction with p53. A, Silver-stained SDS gel from Flag-peptide based elution. Sequence of the p53 protein (lower panel) (SEQ ID NO:1) with matching peptides by mass spectrometry, underlined. B, COP1 interacts with exogenous p53 in vivo. Saos-2 cells were transfected, immunoprecipitated and immunoblotted (western blot, WB) as indicated. C, COP1 interacts with endogenous p53 in vivo. U2-OS cells were transfected with or without COP1, immunoprecipitated and immunoblotted as indicated. D, Endogenous p53 interacts with endogenous COP1. U2-OS cells were immunoprecipitated with anti-p53 or anti-Myc, and immunoblotted with anti-COP1. E, COP1 interacts with p53 in vitro. GST or GST-p53 was incubated with in vitro translated HA-COP1, and bound COP1 was detected by anti-HA immunoblotting. The lower panel represents 20% total input of HA-COP1.

The present invention, in part, demonstrates that COP1 is overexpressed in a variety of cancers and identifies the tumor suppressor protein, p53, as a COP1-interacting protein. Functionally, COP1 degrades p53 via the proteasome, directly ubiquitinates p53 in vivo in an MDM2-independent manner, and in vitro, inhibits p53 transactivation potential, and inhibits p53-induced apoptosis. In addition, siRNA ablation of COP1 stabilizes p53 and increases transactivation of the downstream target gene, p21, consequently arresting cells in G1 phase of the cell cycle. COP1 was also identified as a p53-inducible gene which participates in an autoregulatory feedback loop. Furthermore, cancers that overexpress COP1 show a decrease in p21 mRNA.

Accordingly, overexpression of COP1 may be used to diagnose a variety of cancers or cell types. In some embodiments, overexpression of COP1 in cells or tissue that express wild type p53 is diagnostic of cancer.

Various alternative embodiments and examples of the invention are described herein. These embodiments and examples are illustrative and should not be construed as limiting the scope of the invention.

Abnormal Cell Proliferation

The terms "cell proliferative disorder" and "proliferative disorder" refer to disorders that are associated with some degree of abnormal cell proliferation. In one embodiment, the cell proliferative disorder is cancer.

By a "cancer", "neoplasm", "neoplasia", "carcinoma", "cancerous" or "tumor" is meant to refer to or describe the physiological condition in mammals that is typically characterized by unregulated cell growth. In general, a cell of a neoplasm or cancer e.g., a neoplastic cell, has been released from normal cell division control, i.e., a cell whose growth or proliferation is not regulated by the ordinary biochemical and physical influences in the cellular environment, and exhibits characteristics of unregulated growth, local tissue invasion, metastasis, etc. Generally, a neoplastic cell proliferates to form a clone of cells which are either benign or malignant. The term cancer or neoplasm therefore includes cell growths that are technically benign but which carry the risk of becoming malignant. By "malignancy" is meant an abnormal growth or proliferation of any cell type or tissue. Malignant cells or tissue may inhibit anaplasia or loss of differentiation/orientation, when compared to a normal cell or tissue of the same type, and may exhibit invasion and metastasis capabilities.

"Tumor", as used herein, refers to all neoplastic cell growth and proliferation, whether malignant or benign, and all pre-cancerous and cancerous cells and tissues.

Most cancers fall within three broad histological classifications: carcinomas, which are the predominant cancers and are cancers of epithelial cells or cells covering the external or internal surfaces of organs, glands, or other body structures (e.g., skin, uterus, lung, breast, prostate, stomach, bowel), and which tend to mestastasize; sarcomas, which are derived from connective or supportive tissue (e.g., bone, cartilage, tendons, ligaments, fat, muscle); and hematologic tumors, which are derived from bone marrow and lymphatic tissue. Carcinomas may be adenocarcinomas (which generally develop in organs or glands capable of secretion, such as breast, lung, colon, prostate or bladder) or may be squamous cell carcinomas (which originate in the squamous epithelium and generally develop in most areas of the body). Sarcomas may be osteosarcomas or osteogenic sarcomas (bone), chondrosarcomas (cartilage), leiomyosarcomas (smooth muscle), rhabdomyosarcomas (skeletal muscle), mesothelial sarcomas or mesotheliomas (membranous lining of body cavities), fibrosarcomas (fibrous tissue), angiosarcomas or hemangioendotheliomas (blood vessels), liposarcomas (adipose tissue), gliomas or astrocytomas (neurogenic connective tissue found in the brain), myxosarcomas (primitive embryonic connective tissue), mesenchymous or mixed mesodermal tumors (mixed connective tissue types). Hematologic tumors may be myelomas, which originate in the plasma cells of bone marrow; leukemias which may be "liquid cancers" and are cancers of the bone marrow and may be myelogenous or granulocytic leukemia (myeloid and granulocytic white blood cells), lymphatic, lymphocytic, or lymphoblastic leukemias (lymphoid and lymphocytic blood cells) e.g., acute lymphoblastic leukemia, chronic lymphocytic leukemia, acute monocytic leukemia, acute promyelocytic leukemia, chronic myelocytic leukemia, etc., or polycythemia vera or erythremia (various blood cell products, but with red cells predominating); or lymphomas, which may be solid tumors and which develop in the glands or nodes of the lymphatic system, and which may include Hodgkin or Non-Hodgkin lymphomas, Burkitt's lymphoma, etc. In addition, mixed type cancers, such as adenosquamous carcinomas, mixed mesodermal tumors, carcinosarcomas, or teratocarcinomas also exist.

Cancers may also be named based on the organ in which they originate i.e., the "primary site," for example, cancer of the breast, brain, lung, liver, skin, prostate, testicle, bladder, colon and rectum, cervix, uterus, etc. This naming persists even if the cancer metastasizes to another part of the body, that is different from the primary site, and cancers according to the invention include primary cancers, as well as cancers that have metastasized.

Cancers named based on primary site may be correlated with histological classifications. For example, lung cancers are generally small cell lung cancers or non-small cell lung cancers, which may be squamous cell carcinoma, adenocarcinoma, or large cell carcinoma; skin cancers are generally basal cell cancers, squamous cell cancers, or melanomas e.g., malignant melanoma. Lymphomas may arise in the lymph nodes associated with the head, neck and chest, as well as in the abdominal lymph nodes or in the axillary or inguinal lymph nodes. Identification and classification of types and stages of cancers may be performed by using for example information provided by the Surveillance, Epidemiology, and End Results (SEER) Program of the National Cancer Institute, which is an authoritative source of information on cancer incidence and survival in the United States and is recognized around the world. The incidence and survival data of the SEER Program may be used to access standard survival for a particular cancer site and stage. For example, to ensure an optimal comparison group, specific criteria may be selected from the database, including date of diagnosis and exact stage. Identification of cancers may also be performed by using for example information provided in diagnostic manuals such as The Merck Manual of Diagnosis and Therapy, 17.sup.th edition, M. H. Beers and R. Barkow, eds., John Wiley and Sons, 1999.

Examples of cancers or neoplasms may also include, without limitation, transformed and immortalized cells, solid tumors, myeloproliferative diseases, blastomas, squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, serous adenocarcinoma, endometrioid adenocarcinoma, clear cell adenocarcinoma, mucinous adenocarcinoma, Brenner tumor, teratoma, dysgerminoma, choriocarcinoma, fibroma, granulosa cell tumor, Sertoli-Leydig cell tumor, undifferentiated ovarian carcinoma, salivary gland carcinoma, kidney or renal cancer, prostate cancer, vulval cancer, thyroid cancer, hepatic carcinoma, anal carcinoma, penile carcinoma, cancer of the head and/or neck, Ewing's sarcoma, hemangiosarcoma, Kaposi's sarcoma, liposarcoma, peripheral neuroepithelioma, synovial sarcoma, Hodgkin's disease, etc. as known in the art.

Cancers according to the invention include any cancer in which the cancer cells or tissue overexpress COP1 molecules or in which COP1 activity is upregulated. In some embodiments, cancers according to the invention include any cancer in which the cancer cells or tissue also express wild type p53 molecules.

Polypeptides, Nucleic Acid Molecules, and Test Compounds

Compounds according to the invention include, without limitation, COP1 and p53 nucleic acid molecules, polypeptides and/or analogues, variants, homologs and fragments thereof. Such compounds may be used in any of the diagnostic, prognostic, therapeutic, screening, etc. methods of the invention. Compounds can be prepared by, for example, replacing, deleting, or inserting an amino acid residue at any position of a COP1 or p53 peptide or peptide analogue, with other conservative amino acid residues, i.e., residues having similar physical, biological, or chemical properties, or with non-conservative amino acid residues and screening for the ability of the compound to mediate binding to p53 (if the compound is a COP1 molecule) or to COP1 (if the compound is a p53 molecule). In some embodiments, compounds according to the invention may be MDM2, Pirh2, or p21 molecules. In some embodiments, compounds of the invention include antibodies that specifically bind to COP1 or p53 e.g., to mutant or wild type p53. Such antibodies may be for example humanized antibodies.

An antibody "specifically binds" an antigen when it recognises and binds the antigen, but does not substantially recognise and bind other molecules in a sample. For example, a COP1 antibody specifically binds a COP1 molecule, but does not substantially bind any other molecule such as those present in a cancer cell or tissue. In some embodiments, a COP1 antibody may specifically bind a human COP1 molecule and may not specifically bind COP1 molecules from other species. In another example, a p53 antibody specifically binds a p53 molecule, but does not substantially bind any other molecule such as those present in a cancer cell or tissue. In some embodiments, a p53 antibody may specifically bind a human p53 molecule and may not specifically bind p53 molecules from other species. In some embodiments, a p53 antibody may specifically bind a mutant p53 molecule and may not specifically bind a wild type p53 molecule. In some embodiments, a p53 antibody may specifically bind a wild type p53 molecule and may not specifically bind a mutant p53 molecule. An antibody that specifically binds an antigen has, for example, an affinity for the antigen which is at least 10, 100, 1000 or 10000 times greater than the affinity of the antibody for another reference molecule in a sample.

A "COP1 molecule" as used herein refers to a molecule substantially identical to: a COP1 polypeptide; a nucleic acid molecule encoding a COP1 polypeptide; a COP1 nucleic acid molecule; as well as isoforms, fragments, analogs, or variants thereof. For example, a COP1 molecule can include an isoform, fragment, analog, or variant of a COP1 polypeptide derived from a mammal that has the ability to bind p53 and/or the COP1 ligase activity.

A COP1 molecule can include, without limitation, polypeptide or nucleic acid molecules containing sequences substantially identical to those set forth in Accession Nos. AAH82804 (mouse), NP_036061 (mouse), NP_001001740 (human, isoform d24), NP_071902 (human, isoform a), XP_468011 (Oryza sativa), XP_468010 (Oryza sativa), XP_463866 (Oryza sativa), AAM34692 (human), AAH39723 (human), BAB45239 (human), P_ABG08243 (human), AAD51094 (mouse), AAN86553 (Brassica rapa subsp. Pekinensis), CAA98718 (Saccharomyces cerevisiae), CAA04168 (Arabidopsis thaliana), XM_477896 (Oryza sativa), XM_479164 (Oryza sativa), BK000438 (human), AF508940 (human), AF151110 (mouse), L24437 (Arabidopsis thaliana), P_AAY60008 (human), P_ABJ19398 (human), P_ABB11576(human), P_ABG95247 (human), P_AAW74797 (human), P_ABP69180 (human), P_AAB92798 (human), XP_064815 (human), and/or P_AAG02591 (human), as well as isoforms, fragments, analogs, or variants thereof. A COP1 molecule can be a molecule as described in Bianchi et al.,[30] Wang et al.,[39] or Yi et al.[20] A COP1 molecule can include molecules comprising sequences corresponding to domains of COP1, for example, residues 136-177 of Accession No. NP_071902 (the RING domain); residues 231-306 of Accession No. NP_071902 (the coiled-coiled domain); and/or residues 410-727 of Accession No. NP_071902 (the WD40 domain). In some embodiments, a COP1 polypeptide includes a molecule substantially identical to the sequences set forth herein that is capable of directly binding a p53 polypeptide and/or inhibiting p53 activity or function. Without being bound to any particular hypothesis, COP1 polypeptides may form homodimers to negatively regulate p53. Accordingly, a COP1 molecule may include a molecule substantially identical to the sequences set forth herein that is capable of homodimerization. In some embodiments, COP1 polypeptide or nucleic acid molecules having the sequences set forth herein may be specifically excluded from certain methods according to the invention, e.g., methods of diagnosing a specific cancer, e.g., a breast cancer, by detecting COP1 expression levels.

"p53" is a potent tumor suppressor protein[26,27] encoding a 393 amino acid phosphoprotein. p53 is negatively regulated or mutated in many cancers.[40-43] Absence or inactivation of p53 may contribute to cancer. A wide variety of p53 mutations exist. A "wild type" p53 is p53 found in normal (i.e., non-cancerous cells) or p53 that does not have a mutation correlated to a cancer. The p53 status of a sample (e.g., whether the sample includes wild type or mutant p53) may be assessed as for example described in U.S. Pat. No. 6,090,566 issued to Vogelstein et al., or using standard techniques such as described herein or known in the art. A p53 molecule may include, without limitation, polypeptides containing sequences substantially identical to that set forth in for example Accession No. P04637 and nucleic acid molecules encoded by those sequences.

MDM2 or Pirh2 molecules include ligases[7-10] which transfer ubiquitin from an E2 enzyme, such as UbCH5b, to a substrate on multiple lysine residues, or upon substrate-conjugated ubiquitin to generate a polyubiquitin chain and are negative regulators of p53.[7,25] MDM2 or Pirh2 molecules include molecules having sequences that are substantially identical to those set forth in Accession Nos. AF527840 (MDM2) and AF255666 (Pirh2) and nucleic acid molecules encoded by those sequences.

p21 or "WAF1/Cip1" was originally described as a universal inhibitor of cyclin-dependent kinases. It is induced by both p53-dependent and p53-independent mechanisms and has been implicated as an inhibitor of cell proliferation. P21 molecules include molecules having sequences substantially identical to those set forth in Accession No. U03106 and nucleic acid molecules encoded by those sequences.

A "substantially identical" sequence is an amino acid or nucleotide sequence that differs from a reference sequence only by one or more conservative substitutions, as discussed herein, or by one or more non-conservative substitutions, deletions, or insertions located at positions of the sequence that do not destroy the biological function of the amino acid or nucleic acid molecule. Such a sequence can be any integer from 10% to 99%, or more generally at least 10%, 20%, 30%, 40%, 50, 55% or 60%, or at least 65%, 75%, 80%, 85%, 90%, or 95%, or as much as 96%, 97%, 98%, or 99% identical when optimally aligned at the amino acid or nucleotide level to the sequence used for comparison using, for example, the Align-2 Program developed by Genentech. For polypeptides, the length of comparison sequences may be at least 2, 5, 10, or 15 amino acids, or at least 20, 25, or 30 amino acids. In alternate embodiments, the length of comparison sequences may be at least 35, 40, or 50 amino acids, or over 60, 80, or 100 amino acids. For nucleic acid molecules, the length of comparison sequences may be at least 5, 10, 15, 20, or 25 nucleotides, or at least 30, 40, or 50 nucleotides. In alternate embodiments, the length of comparison sequences may be at least 60, 70, 80, or 90 nucleotides, or over 100, 200, or 500 nucleotides.

"Percent (%) amino acid sequence identity" as herein is defined as the percentage of amino acid residues in a candidate sequence that are identical with the amino acid residues in a selected sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST (National Library of Medicine software), BLAST-2, ALIGN, ALIGN-2, Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

Alternatively, or additionally, two nucleic acid sequences may be "substantially identical" if they hybridize under high stringency conditions. "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995), which is hereby incorporated by reference.

According to one embodiment, the hybridization is under high stringency conditions. "Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50C; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42C; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42C, with a 10 minute wash at 42C in 0.2×SSC (sodium chloride/sodium citrate) followed by a 10 minute high-stringency wash consisting of 0.1×SSC containing EDTA at 55C.

"Moderately stringent conditions" can be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50C. The skilled artisan will recognize how to adjust the temperature, ionic strength, etc. as necessary to accommodate factors such as probe length and the like.

Hybridizations may be carried out over a period of about 20 to 30 minutes, or about 2 to 6 hours, or about 10 to 15 hours, or over 24 hours or more. High stringency hybridization is also relied upon for the success of numerous techniques routinely performed by molecular biologists, such as high stringency PCR, DNA sequencing, single strand conformational polymorphism analysis, and in situ hybridization. In contrast to northern and Southern hybridizations, these techniques are usually performed with relatively short probes (e.g., usually about 16 nucleotides or longer for PCR or sequencing and about 40 nucleotides or longer for in situ hybridization).

It is well known in the art that some modifications and changes can be made in the structure of a polypeptide without substantially altering the biological function of that peptide, to obtain a biologically equivalent polypeptide. In one aspect of the invention, polypeptides of the present invention also extend to biologically equivalent peptides that differ from a portion of the sequence of the polypeptides of the present invention by amino acid substitutions that do not affect biological function.

As used herein, the term "conserved amino acid substitutions" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

As used herein, the term "amino acids" means those L-amino acids commonly found in naturally occurring proteins, D-amino acids and such amino acids when they have been modified. Accordingly, amino acids of the invention may include, for example: 2-Aminoadipic acid; 3-Aminoadipic acid; beta-Alanine; beta-Aminopropionic acid; 2-Aminobutyric acid; 4-Aminobutyric acid; piperidinic acid; 6-Aminocaproic acid; 2-Aminoheptanoic acid; 2-Aminoisobutyric acid; 3-Aminoisobutyric acid; 2-Aminopimelic acid; 2,4 Diaminobutyric acid; Desmosine; 2,2'-Diaminopimelic acid; 2,3-Diaminopropionic acid; N-Ethylglycine; N-Ethylasparagine; Hydroxylysine; allo-Hydroxylysine; 3-Hydroxyproline; 4-Hydroxyproline; Isodesmosine; allo-Isoleucine; N-Methylglycine; sarcosine; N-Methylisoleucine; 6-N-methyllysine; N-Methylvaline; Norvaline; Norleucine; and Ornithine.

In some embodiments, conserved amino acid substitutions may be made where an amino acid residue is substituted for another having a similar hydrophilicity value (e.g., within a value of plus or minus 2.0, or plus or minus 1.5, or plus or minus 1.0, or plus or minus 0.5), where the following may be an amino acid having a hydropathic index of about −1.6 such as Tyr (−1.3) or Pro (−1.6) are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); H is (−0.5); Cys (−1.0); Met (−1.3); Val (−1.5); Leu (−1.8); Ile (−1.8); Tyr (−2.3); Phe (−2.5); and Trp (−3.4).

In alternative embodiments, conservative amino acid substitutions may be made where an amino acid residue is substituted for another having a similar hydropathic index (e.g., within a value of plus or minus 2.0, or plus or minus 1.5, or plus or minus 1.0, or plus or minus 0.5). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conservative amino acid substitutions may be made using publicly available families of similarity matrices (Altschul, S. F. 1991. "Amino acid substitution matrices from an information theoretic perspective." Journal of Molecular Biology, 219: 555-665; Dayhoff, M. O., Schwartz, R. M., Orcutt, B. C. 1978. "A model of evolutionary change in proteins." In "Atlas of Protein Sequence and Structure" 5(3) M. O. Dayhoff (ed.), 345-352, National Biomedical Research Foundation, Washington; States, D. J., Gish, W., Altschul, S. F. 1991. "Improved Sensitivity of Nucleic Acid Database Search Using Application-Specific Scoring Matrices" Methods: A companion to Methods in Enzymology 3(1): 66-77; Steven Henikoff and Jorja G. Henikoff. 1992 "Amino acid substitution matrices from protein blocks." Proc. Natl. Acad. Sci. USA. 89(biochemistry): 10915-10919; M. S. Johnson and J. P. Overington. 1993. "A Structural Basis of Sequence Comparisons: An evaluation of scoring methodologies." Journal of Molecular Biology. 233: 716-738. Steven Henikoff and Jorja G. Henikoff. 1993. "Performance Evaluation of Amino Acid Substitution Matrices." Proteins: Structure, Function, and Genetics. 17: 49-61; Karlin, S, and Altschul, S. F. 1990. "Methods for assessing the statistical significance of molecular sequence features by using general scoring schemes" Proc. Natl. Acad. Sci. USA. 87: 2264-2268.) The PAM matrix is based upon counts derived from an evolutionary model, while the Blosum matrix uses counts derived from highly conserved blocks within an alignment. A similarity score of above zero in either of the PAM or Blosum matrices may be used to make conservative amino acid substitutions.

In alternative embodiments, conservative amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In alternative embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (*J. Mol. Bio.* 179:125-142, 184). Genetically encoded hydrophobic amino acids include Gly, Ala, Phe, Val, Leu, Ile, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR, etc., where R is independently (C$_1$-C$_6$) alkyl, substituted (C$_1$-C$_6$) alkyl, (C$_1$-C$_6$) alkenyl, substituted (C$_1$-C$_6$) alkenyl, (C$_1$-C$_6$) alkynyl, substituted (C$_1$-C$_6$) alkynyl, (C$_5$-C$_{20}$) aryl, substituted (C$_5$-C$_{20}$) aryl, (C$_6$-C$_{26}$) alkaryl, substituted (C$_6$-C$_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Trp, while non-genetically encoded aromatic amino acids include phenylglycine, 2-napthylalanine, beta-2-thienylalanine, 1,2,3,4-tetrahydroisoquinoline-3-carboxylic acid, 4-chlorophenylalanine, 2-fluorophenylalanine-3-fluorophenylalanine, and 4-fluorophenylalanine.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met, while non-genetically encoded apolar amino acids include cyclohexylalanine. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile, while non-genetically encoded aliphatic amino acids include norleucine.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln, while non-genetically encoded polar amino acids include citrulline, N-acetyl lysine, and methionine sulfoxide.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His, while non-genetically encoded basic amino acids include the non-cyclic amino acids ornithine, 2,3,-diaminopropionic acid, 2,4-diaminobutyric acid, and homoarginine.

It will be appreciated by one skilled in the art that the above classifications are not absolute and that an amino acid may be classified in more than one category. In addition, amino acids can be classified based on known behaviour and or characteristic chemical, physical, or biological properties based on specified assays or as compared with previously identified amino acids. Amino acids can also include bifunctional moieties having amino acid-like side chains.

Conservative changes can also include the substitution of a chemically derivatised moiety for a non-derivatised residue, by for example, reaction of a functional side group of an amino acid. Thus, these substitutions can include compounds whose free amino groups have been derivatised to amine hydrochlorides, p-toluene sulfonyl groups, carbobenzoxy groups, t-butyloxycarbonyl groups, chloroacetyl groups or formyl groups. Similarly, free carboxyl groups can be derivatized to form salts, methyl and ethyl esters or other types of esters or hydrazides, and side chains can be derivatized to form O-acyl or O-alkyl derivatives for free hydroxyl groups or N-im-benzylhistidine for the imidazole nitrogen of histidine. Peptide analogues also include amino acids that have been chemically altered, for example, by methylation, by amidation of the C-terminal amino acid by an alkylamine such as ethylamine, ethanolamine, or ethylene diamine, or acylation or methylation of an amino acid side chain (such as acylation of the epsilon amino group of lysine). Peptide analogues can also include replacement of the amide linkage in the peptide with a substituted amide (for example, groups of the formula —C(O)—NR, where R is ($C_1$-$C_6$) alkyl, ($C_1$-$C_6$) alkenyl, ($C_1$-$C_6$) alkynyl, substituted ($C_1$-$C_6$) alkyl, substituted ($C_1$-$C_6$) alkenyl, or substituted ($C_1$-$C_6$) alkynyl) or isostere of an amide linkage (for example, —$CH_2$NH—, —$CH_2$S, —$CH_2CH_2$—, —CH=CH— (cis and trans), —C(O)$CH_2$—, —CH(OH)$CH_2$—, or —$CH_2$SO—).

The compound can be covalently linked, for example, by polymerisation or conjugation, to form homopolymers or heteropolymers. Spacers and linkers, typically composed of small neutral molecules, such as amino acids that are uncharged under physiological conditions, can be used. Linkages can be achieved in a number of ways. For example, cysteine residues can be added at the peptide termini, and multiple peptides can be covalently bonded by controlled oxidation. Alternatively, heterobifunctional agents, such as disulfide/amide forming agents or thioether/amide forming agents can be used. The compound can also be linked to a another compound that can for example, target cancer cells or inhibit the growth or proliferation of cancer cells. The compound can also be constrained, for example, by having cyclic portions.

Peptides or peptide analogues can be synthesised by standard chemical techniques, for example, by automated synthesis using solution or solid phase synthesis methodology. Automated peptide synthesisers are commercially available and use techniques well known in the art. Peptides and peptide analogues can also be prepared using recombinant DNA technology using standard methods such as those described in, for example, Sambrook, et al. (Molecular Cloning: A Laboratory Manual. $2^{nd}$ ed., Cold Spring Harbor Laboratory, Cold Spring Harbor Laboratory Press, Cold Spring Harbor, N.Y., 1989) or Ausubel et al. (Current Protocols in Molecular Biology, John Wiley & Sons, 1994).

In some embodiments, compounds of the invention include nucleic acid molecules that are substantially identical to COP1, MDM2, p21, or p53 nucleic acid molecules or fragments thereof, or are complementary to COP1, MDM2, p21, or p53 nucleic acid molecules or fragments thereof. Such nucleic acid molecules may be used for example as probes or primers in the assays and methods of the invention. A "probe" or "primer" is a single-stranded DNA or RNA molecule of defined sequence that can base pair to a second DNA or RNA molecule that contains a complementary sequence (the target). The stability of the resulting hybrid molecule depends upon the extent of the base pairing that occurs, and is affected by parameters such as the degree of complementarity between the probe and target molecule, and the degree of stringency of the hybridization conditions. The degree of hybridization stringency is affected by parameters such as the temperature, salt concentration, and concentration of organic molecules, such as formamide, and is determined by methods that are known to those skilled in the art. Probes or primers specific for the nucleic acid sequences described herein, or portions thereof, may vary in length by any integer from at least 8 nucleotides to over 500 nucleotides, including any value in between, depending on the purpose for which, and conditions under which, the probe or primer is used. For example, a probe or primer may be 8, 10, 15, 20, or 25 nucleotides in length, or may be at least 30, 40, 50, or 60 nucleotides in length, or may be over 100, 200, 500, or 1000 nucleotides in length. Probes or primers specific for the nucleic acid molecules described herein may have greater than 20-30% sequence identity, or at least 55-75% sequence identity, or at least 75-85% sequence identity, or at least 85-99% sequence identity, or 100% sequence identity to the nucleic acid sequences described herein.

Probes or primers may be derived from genomic DNA or cDNA, for example, by amplification, or from cloned DNA segments, and may contain either genomic DNA or cDNA sequences representing all or a portion of a single gene from a single individual. A probe may have a unique sequence (e.g., 100% identity to a COP1 or p53 nucleic acid molecule) and/or have a known sequence. Probes or primers may be chemically synthesized.

Probes or primers can be detectably-labeled, either radioactively or non-radioactively, by methods that are known to those skilled in the art. Probes or primers can be used for methods involving nucleic acid hybridization, such as nucleic acid sequencing, nucleic acid amplification by the polymerase chain reaction, single stranded conformational polymorphism (SSCP) analysis, restriction fragment polymorphism (RFLP) analysis, Southern hybridization, northern hybridization, in situ hybridization, electrophoretic mobility shift assay (EMSA), and other methods that are known to those skilled in the art.

Nucleic acid molecules may also be antisense molecules, siRNA molecules, or triple helix molecules that may be used for example to reduce expression of the target molecule in a cell. By "antisense," as used herein in reference to nucleic acids, is meant a nucleic acid sequence that is complementary to the coding strand of a nucleic acid molecule, for example, a gene, such as a COP1, mdm2, p21, or p53 gene. In some embodiments, an antisense nucleic acid molecule is one which is capable of lowering the level of polypeptide encoded by the complementary gene when both are expressed in a cell. In some embodiments, the polypeptide level is lowered by any value from at least 10% to at least 25%, or by any value from at least 25% to at least 50%, or by any value from at least 50% to at least 75%, or by any value from at least 75% to 100%, or by any value from at least 2-fold to at least 10-fold, or by 100-fold, as compared to the polypeptide level in a cell expressing only the gene, and not the complementary antisense nucleic acid molecule.

An "siRNA" molecule or an "RNAi molecule refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length. See also PCT/US03/07237, herein incorporated by reference in its entirety. An siRNA molecule or RNAi molecule is "specific" for a target nucleic acid if it reduces expression of the nucleic acid by at least about 10% when the siRNA or RNAi is expressed in a cell that expresses the target nucleic acid.

It is understood that therapeutic agents discussed herein, including nucleic acid molecules, can be modified or synthesized to improved their bioavailability, pharmacokinetic and pharmacodynamic properties. For example, therapeutic nucleic acid molecules can be synthesized with one or more phosphorothioate linkages using techniques known in the art.

In some embodiments, test compounds include small organic molecules. A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons. A small organic molecule may be a ubiquitin ligase inhibitor, for example, Ro106-9920 and analogs thereof.[44]

In some embodiments of the invention, test compounds include antibodies that are capable of interfering with COP1/p53 interaction or binding. Test compounds may also include peptides, nucleic acid molecules, or small molecules, that are capable of interfering with COP1/p53 interaction or binding and/or inhibit COP1 activity (e.g., COP1 enzymatic activity).

Candidate or test compounds may be identified from large libraries of both natural products or synthetic (or semi-synthetic) extracts or chemical libraries according to methods known in the art. Those skilled in the field of drug discovery and development will understand that the precise source of test extracts or compounds is not critical to the method(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available. Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla., USA), and PharmaMar, MA, USA. In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

When a crude extract is found to, for example, inhibit COP1/p53 interaction, further fractionation of the positive lead extract may be necessary to isolate chemical constituents responsible for the observed effect. Thus, the goal of the extraction, fractionation, and purification process is the careful characterization and identification of a chemical entity within the crude extract having COP1/p53 binding inhibitory activities. The same assays described herein for the detection of activities in mixtures of compounds can be used to purify the active component and to test derivatives thereof. Methods of fractionation and purification of such heterogeneous extracts are known in the art. If desired, compounds shown to be useful agents for treatment are chemically modified according to methods known in the art. Compounds identified as being of therapeutic, prophylactic, diagnostic, or other value may be subsequently analyzed using, for example, any animal model for cancer.

Diagnostic, Therapeutic, Prophylactic and/or Screening Uses, Assays, and Reagents Compounds, compositions (e.g., pharmaceutical compositions), and methods according to the invention may be used to diagnose cancer or to treat or prevent cancer in a subject, or to screen test compounds useful for treating or preventing cancer.

As used herein, a subject may be a human, non-human primate, rat, mouse, cow, horse, pig, sheep, goat, dog, cat, fly, worm, etc. The subject may be a clinical patient, a clinical trial volunteer, an experimental animal, etc. The subject may be suspected of having or being at risk for having a cancer, be diagnosed with a cancer, or be a control subject that is confirmed to not have a cancer. In one preferred embodiment, the subject is a human.

Diagnostic methods for cancer and the clinical delineation of cancer diagnoses are known to those of ordinary skill in the art. As discussed herein, a variety of cancers may be diagnosed or detected by measuring COP1 expression levels, where the overexpression of COP1 indicates a cancer diagnosis. By "overexpression" is meant an increase in mRNA or polypeptide expression of a particular molecule e.g., COP1, relative to a control e.g., relative to the level of expression that is normally produced by non-cancerous cells. Cancers which exhibit overexpression of a COP1 molecule may also exhibit reduced expression of a p53 molecule (e.g., a p53 polypeptide) or reduced expression of a p21 molecule (e.g., a p21 mRNA). By a "reduction in expression levels" is meant a decrease in mRNA or polypeptide expression of a particular molecule e.g., p53 or p21, relative to a control e.g., relative to the level of expression that is normally produced by non-cancerous cells. Such an increase or decrease may be of any value between 10% and 90%, or of any value between 30% and 60%, or over 100%, or may be a change of any value between 2-fold to 10-fold, inclusive, or more e.g., 100-fold, when compared to a control. The exact amount of overexpression or increase, or reduction or decrease, is not critical, as long as the overexpression or reduction is statistically significant.

Reagents according to the invention include compounds as described herein. In some embodiments, the invention encompasses cells, e.g., mammalian cells, that include compounds as described herein. For example, a mammalian cell can be engineered by for example recombinant techniques to include recombinant p53, recombinant Pirh2, recombinant MDM2, and/or recombinant COP1 molecules or to reduce or knockout endogenous protein expression or to mutate those proteins by altering the genes that encode those proteins. The expression level or activity of these molecules may be reduced by for example using siRNA molecules specifically directed against these molecules. Such mammalian cells may for example be used to screen for test compounds that interfere with p53/COP1 binding or inhibit p53 or COP1 activity.

For example, for screening test compounds for use in treating a cancer or a cell proliferative disorder, a control cell could express reduced or zero levels of p53 and express normal or increased levels of COP1. A test cell could express normal or increased levels of both COP1 and p53. Such cells could be incubated with a test compound and assayed for changes in cell cycle, p21 expression, p53 induced apoptosis, p53 dependent transactivation, COP1 ligase activity, etc. Reporter based constructs such as p21-Luciferase could be used, with an internal luciferase reporter as a background as well as real-time RT-PCR techniques. Such mammalian cells could be engineered in existing cell lines such as for example a p53 wild-type cell line (U2-OS cells), or a p53 null cell line (H1299) which can be engineered to overexpress COP1 molecules.

Assays according to the invention may be carried out in vivo, in vitro, or ex vivo. using samples obtained from standard sources and by standard procedures. A "sample" can be any organ, tissue, cell, or cell extract isolated from a subject, such as a sample isolated from a mammal having a cancer. For example, a sample can include, without limitation, cells or tissue (e.g., from a biopsy or autopsy) from bone, brain, breast, colon, muscle, nerve, ovary, prostate, retina, skin, skeletal muscle, intestine, testes, heart, liver, kidney, stomach, pancreas, uterus, adrenal gland, tonsil, spleen, soft tissue, peripheral blood, whole blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, urine, stool, saliva, cerebrospinal fluid, pericardial fluid, peritoneal fluid, placental extracts, amniotic fluid, a cryoprecipitate, a cryosupernatant, a cell lysate, mammalian cell culture or culture medium, products of fermentation, ascitic fluid, proteins present in blood cells, solid tumours, or any other specimen, or any extract thereof, obtained from a patient (human or animal), test subject, or experimental animal. In some embodiments, it may be desirable to separate cancerous cells from non-cancerous cells in a sample.

A sample may also include, without limitation, products produced in cell culture by normal or transformed cells (e.g., via recombinant DNA or monoclonal antibody technology). A sample may also include, without limitation, any organ, tissue, cell, or cell extract isolated from a non-mammalian subject, such as an insect or a worm. A "sample" may also be a cell or cell line created under experimental conditions, that is not directly isolated from a subject. A sample can also be cell-free, artificially derived or synthesised. A sample may be from a cell or tissue known to be cancerous, suspected of being cancerous, or believed not be cancerous (e.g., normal or control).

A "control" includes a sample obtained for use in determining base-line expression or activity. Accordingly, a control sample may be obtained by a number of means including from non-cancerous cells or tissue e.g., from cells surrounding a tumor or cancerous cells of a subject; from subjects not having a cancer; from subjects not suspected of being at risk for a cancer; or from cells or cell lines derived from such subjects. A control also includes a previously established standard. Accordingly, any test or assay conducted according to the invention may be compared with the established standard and it may not be necessary to obtain a control sample for comparison each time. In an in vitro ubiquitination assay, a control can be a COP1 molecule that has reduced ability to ubiquitinate a p53 molecule (e.g., a molecule that is defective in its ligase domain such as COP1ΔRing).

For example, COP1 or p53 molecules may be provided in cancer cells, tissues, or cell lysates, or may be constructed using recombinant techniques. Microarrays, for example, tissue microarrays may be used. Recombinant proteins, cells and/or cell lines may be obtained from commercial sources, for example, ATCC, Manassas, Va., USA for cells or cell lines.

Suitable animal models for cancer may be obtained from, for example, The Jackson Laboratory, Bar Harbor, Me., USA. In some embodiments, an animal model having defects in COP1 or p53 expression or activity may be used.

COP1 or p53 nucleic acid molecule or polypeptide expression or activity, or COP1/p53 binding, can be assayed using a variety of techniques, including immunohistochemistry (IHC), in situ hybridization (ISH), Northern blotting, polymerase chain reaction (e.g., real time quantitative PCR or RT-PCR), antibody based assays, such as immunoprecipitation, immunofluorescence, Western blotting, nucleic acid sequencing etc. For example, methods such as sequencing, single-strand conformational polymorphism (SSCP) analysis, or restriction fragment length polymorphism (RFLP) analysis of PCR products derived from a sample can be used to detect a mutation in a COP1 or p53 gene; immunoprecipitation, RIA, ELISA or western blotting can be used to measure levels of COP1 or p53 polypeptide or binding; expression of a COP1 or p53 gene or mRNA may be downregulated using antisense oligonucleotides, siRNA, or triple-strand forming oligonucleotides to inhibit transcription or translation; northern blotting can be used to measure COP1 or p53 mRNA levels, or PCR can be used to measure the level of a COP1 or p53 nucleic acid molecule. Such assays include detection of any or all forms of COP1 or p53, including precursors, fragments (e.g., created by endoproteolytic degradation), post-translationally modified forms, etc. The methods of the invention encompass assaying for COP1 related biological activities such as p53 degradation, ubiquitination of p53, inhibition of p53 transactivation, inhibition of p53 induced apoptosis, reduction of p21 mRNA, etc.

In some embodiments, cells in a subject may be exposed in vivo to an antibody (e.g., a COP1 antibody or a p53 antibody or both) which is optionally detectably labeled e.g., radioactive isotope; and binding of the antibody to the cells may be evaluated by e.g., external scanning for radioactivity or analysis of a biopsy.

The assays may be conducted using detectably labelled molecules, i.e., any means for marking and identifying the presence of a molecule, e.g., an oligonucleotide probe or primer, a gene or fragment thereof, a peptide, or a cDNA molecule. Methods for detectably-labelling a molecule are well known in the art and include, without limitation, radioactive labelling (e.g., with an isotope such as $^{32}P$ or $^{35}S$) and nonradioactive labelling such as, enzymatic labelling (for example, using horseradish peroxidase or alkaline phosphatase), chemiluminescent labeling, fluorescent labeling (for example, using fluorescein), bioluminescent labeling, or antibody detection of a ligand attached to the probe. Also included in this definition is a molecule that is detectably labelled by an indirect means, for example, a molecule that is bound with a first moiety (such as biotin) that is, in turn, bound to a second moiety that may be observed or assayed (such as fluorescein-labeled streptavidin). Labels also include digoxigenin, luciferases, and aequorin.

By "detecting" it is intended to include determining the presence or absence of a substance or quantifying the amount of a substance. The term thus refers to the use of the materials, compositions, and methods of the present invention for qualitative and quantitative determinations. In general, the particular technique used for detection is not critical for practice of the invention. For example, "detecting" according to the invention may include detecting: the presence or absence of a COP1, mdm2, p21, orp53 gene, genome, or nucleic acid molecule or a COP1, mdm2, p21, or p53 polypeptide; a mutation in a COP1 mdm2, p21, or p53 gene; a change in expression levels of a COP1, mdm2, p21, or p53 nucleic acid molecule, e.g., mRNA or polypeptide; a change in a biological function/activity of a COP1 polypeptide (e.g., COP1 ligase activity, p53 turnover, repression of p53-dependent transactivation activity) or a p53 polypeptide (e.g., p53 binding, p53-dependent transactivation, COP1 binding, transactivation of p21, etc.), using methods that are known in the art or described below. In some embodiments, "detecting" may include detecting wild type p53. In some embodiments, "detecting" may include detecting mutant p53. Detecting may include quantifying a change (increase or decrease) of any value between 10% and 90%, or of any value between 30% and 60%, or over 100%, when compared to a control. Detecting may include quantifying a change of any value between 2-fold to 10-fold, inclusive, or more e.g., 100-fold.

Pharmaceutical & Veterinary Compositions, Dosages and Administration

Compounds of the invention can be provided alone or in combination with other compounds (for example, nucleic acid molecules, small molecules, peptides, or peptide analogues), in the presence of a liposome, an adjuvant, or any pharmaceutically acceptable carrier, in a form suitable for administration to mammals, for example, humans, mice, etc. If desired, treatment with a compound according to the invention may be combined with more traditional and existing therapies for cancer, such as chemotherapy e.g. alkylating agents, anti-metabolites, antibiotics, anti-microtubule compounds, e.g., Avastin, CPT11, oxaliplatin, radiation therapy, eg. ionizing radiation, etc. In some embodiments, therapeutic compounds according to the invention include siRNA molecules directed against COP1, p53, p21, MDM2, or Pirh2 molecules. Compounds according to the invention may be provided chronically or intermittently. "Chronic" administration refers to administration of the compound(s) continuously for an extended period of time, instead of administering an acute short term dose, so as to maintain the initial therapeutic effect (activity). "Intermittent" administration is treatment that is interspersed with period of no treatment of that particular compound.

Conventional pharmaceutical practice may be employed to provide suitable formulations or compositions to administer the compounds to subjects suffering from or presymptomatic for a cancer. Any appropriate route of administration may be employed, for example, parenteral, intravenous, subcutaneous, intramuscular, intracranial, intraorbital, ophthalmic, intraventricular, intracapsular, intraspinal, intrathecal, intracisternal, intraperitoneal, intranasal, aerosol, topical, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences" (19$^{th}$ edition), ed. A. Gennaro, 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. For therapeutic or prophylactic or preventative compositions, the compounds are administered to an individual in an amount sufficient to prevent, inhibit, or slow a cancer growth or progression, depending on the cancer. Measures of efficacy of the compound include an observable and/or measurable reduction in or absence of one or more of the following: reduction in the number of cancer cells or absence of the cancer cells, reduction in the tumor size; inhibition (i.e., prevent, inhibit, slow, or stop) of cancer cell infiltration into peripheral organs; inhibition (i.e., prevent, inhibit, slow, or stop) of tumor metastasis; inhibition, to some extent, of tumor growth; and/or relief to some extent, one or more of the symptoms associated with the specific cancer, and reduced morbidity and mortality.

An "effective amount" of a compound according to the invention includes a therapeutically effective amount or a prophylactically effective amount. A "therapeutically effective amount" refers to an amount effective, at dosages and for periods of time necessary, to achieve the desired therapeutic result, such as an observable and/or measurable reduction in or absence of one or more of the following: reduction in the number of cancer cells or absence of the cancer cells, reduction in the tumor size; inhibition (i.e., prevent, inhibit, slow, or stop) of cancer cell infiltration into peripheral organs; inhibition (i.e., prevent, inhibit, slow, or stop) of tumor metastasis; inhibition, to some extent, of tumor growth; and/or relief to some extent, one or more of the symptoms associated with the specific cancer, and reduced morbidity and mortality. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as an observable and/or measurable reduction in or absence of one or more of the following: reduction in the number of cancer cells or absence of the cancer cells, reduction in the tumor size; inhibition (i.e., prevent, inhibit, slow, or stop) of cancer cell infiltration into peripheral organs; inhibition (i.e., prevent, inhibit, slow, or stop) of tumor metastasis; inhibition, to some extent, of tumor growth; and/or relief to some extent, one or more of the symptoms associated with the specific cancer, and reduced morbidity and mortality. Typically, a prophylactic dose is used in subjects prior to or at an earlier stage of disease, so that a prophylactically effective amount may be less than a therapeutically effective amount. A preferred range for therapeutically or prophylactically effective amounts of a compound may be any integer from 0.1 nM-0.1M, 0.1 nM-0.05M, 0.05 mM-15 µM or 0.01 nM-10 µM.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In the case of vaccine formulations, an immunogenically effective amount of a compound of the invention can be provided, alone or in combination with other compounds, with an immunological adjuvant, for example, Freund's incomplete adjuvant, dimethyldioctadecylammonium hydroxide, or aluminum hydroxide. The compound may also be linked with a carrier molecule, such as bovine serum albumin or keyhole limpet hemocyanin to enhance immunogenicity.

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

Example 1

Materials and Methods

Expression Vectors, Recombinant Proteins, and Antibodies

Flag-COP1 has been described previously[33]. HA-COP1 was generated by PCR subcloning COP1 into pcDNA3.1+ (Invitrogen), and GST-COP1 was generated by subcloning COP1 into pGEX6P1 (Pharmacia). pcDNA3.1+53, pG13-Luc, p21-Luc, bax-Luc, NS-Luc and pCMV-MDM2 have been described previously[21,22,35].

Full-length COP1 was amplified from cDNA derived from HEK293T cells. HA-COP1 was subcloned by PCR into pcDNA3.1+ (Invitrogen) and GST-COP1 was generated by PCR and subcloned into pGEX6P1 (Pharmacia). COP1-Luc and COP1mut-Luc were generated by ligation of oligonucleotides containing two copies of the p53 consensus site, or containing mutants of the consensus site, derived from the COP1 promoter into pGL3-Promoter (Promega).

All GST recombinant proteins were expressed in *E. coli* strain BL21(DE3) codon+ (Stratagene), sonicated with 1 mg/ml lysozyme, solubilised with 1% TritonX-100 in PBS with protease inhibitor mix (Roche), and subsequently purified using the Glutathione Sepharose 4B batch method and eluted with either reduced glutathione or cleaved with PreScission protease (Pharmacia). In vitro transcription/translation of recombinant protein was carried out using either the T7/T3 coupled TnT Kit (Promega) or Rapid Translation System (RTS) (Roche).

Anti-p53 (DO-1; Calbiochem), anti-p53 (1801; BD Pharmingen), anti-p53 (FL-393; Santa Cruz Biotechnology), anti-p21 (Ab-1; Calbiochem), anti-MDM2 (2A10; Calbiochem), anti-Flag (M2; Sigma), anti-Myc (9E10; Roche), anti-His-HRP (Roche), anti-actin (ICN), anti-GST (B-14; Santa Cruz Biotechnology) and anti-HA (Roche) were used according to manufacturer's recommendations. Anti-COP1 is a monoclonal antibody raised against amino acids 71-270 of human COP1.

Cells, Transfections, Reporter and Apoptosis Assays

U2-OS, Saos-2, HEK293T and BJ cells were purchased from the American Type Culture Collection (ATCC) and maintained in McCoy's 5A (Invitrogen) or DMEM (Sigma) media. $p53^{-/-}/MDM2^{-/-}$ MEFs were grown in DMEM with 10% FBS and 1× L-Glutamine. H1299 cells were grown in RPMI.

All transfections were carried out using Lipofectamine 2000 (Invitrogen), Oligofectamine (Invitrogen) or Geneporter 2 (Gene Therapy Systems) according to manufacturer's recommendations. To assess COP1 effect on steady-state levels of p53, Saos-2 cells were transfected with increasing amounts of FLAG-COP1 or FLAG-COP1ΔRING with 250 or 500 ng pcDNA3.1+p53, or U2-OS cells were transfected with or without increasing amounts (0.5, 1 and 2 µg) of pCMV-FLAG-COP1 or pCMV-FLAG-COP1ΔRING and treated with 50 µM ALLN for 6 hours before harvesting cells where indicated.

For reporter assays, Saos-2 or H1299 cells were transiently transfected with 150 or 250 ng pcDNA3.1+p53 or pcDNA3.1+p53R175H, 100 ngp21-Luc, bax-Luc, COP1-Luc, COP1mut-Luc or NS-Luc, and 10 ng of pCMVβ-Gal, with or without increasing amounts (0.5, 1 and 2 µg) of pCMV-FLAG-COP1 or pCMV-FLAG-COP1ΔRING. Luciferase assays were carried out according to manufacturer's instructions and were normalised to β-galactosidase activity (Promega).

For p53-dependent cell death assays, Saos-2 cells were transiently transfected with 1 µg enhanced green fluorescent protein (EGFP) and 5 µg pcDNA3.1+, pcDNA3.1+p53, pCMV-FLAG-COP1 or pcDNA3.1+p53 and pCMV-FLAG-COP1 for 48 hours. Cells were harvested, and stained with propidium iodide for analysis by fluorescence-activated cell sorting (FACS). Transfected cells were selected and subsequent cell cycle profile determined according to DNA content.

COP1 siRNA1 (AACUGACCAAGAUAACCUUGA) (SEQ ID NO:2), COP1 siRNA1 inverted (AAAGUUCCA-AUAGAACCAGUC) (SEQ ID NO:3), COP1 siRNA2 (AA-GACUUGGAGCAGUGUUACU) (SEQ ID NO:4), COP1 siRNA3 (AAGAGGUGUUGGAGUGUUGAC) (SEQ ID NO:5), Pirh2 siRNA1 (AACTGTGGAATTTGTAGG) (SEQ ID NO:6), Pirh2 B inverted (AAGGAUGUUUAAGGUGU-CAA) (SEQ ID NO:7), Pirh2 siRNA2 (AAUGUAACU-UAUGCCUAGCUA) (SEQ ID NO:8), Pirh2 siRNA2 inverted (AAAUCGAUCCGUAUUCAAUGU) (SEQ ID NO:9) and MDM2 (AAGGAAUUUAGACAACCUGAA) (SEQ ID NO:10) siRNA oligonucleotides with 3Ø dTdT overhangs were synthesized by Genentech or Dharmacon. Control siRNA in experiments refers to a mixture of inverted siRNA oligonucleotides. U2-OS, H1299, Saos-2 and BJ cells were transfected with siRNA oligonucleotides three times at 24-36 h intervals and expanded as necessary to prevent contact inhibition.

Immunoprecipitation and GST-Pull Down Assays

Cells were lysed in immunoprecipitation (IP) lysis buffer (1% Triton X-100, 150 mM NaCl, 50 mM Tris, pH 7.4, and protease inhibitor mix) or radioimmunoprecipitation assay (RIPA) buffer (0.1% SDS, 1% NP-40, 150 mM NaCl, 0.5% deoxycholate, 50 mM Tris, pH 7.4, and protease inhibitor mix), pre-cleared and immunoprecipitated with target antibody and protein A/G PLUS beads. (Pierce). Identification of COP1-interacting proteins was carried out as previously described[33], except that U2-OS cells stably expressing Flag-COP1 were generated.

GST pull down assays were carried out with 5 µg GST or GST-p53 combined with in vitro translated HA-COP1 in PBST (PBS with 0.1% Tween 20) and incubated on ice for 1 hour. Glutathione sepharose 4B beads were then added to the mixture and incubated for 1 hour and subsequently washed 5 times with PBST. GST-bound proteins were subject to SDS-PAGE and immunoblot with anti-HA and anti-GST. IPs were washed in lysis buffer with high salt as required. Pulse-chase experiments were carried out as previously described[7], except that HEK293T cells were transfected with pCMV-Flag6a or pCMV-Flag-COP1 for 24 h, and U2-OS cells were transfected with siRNA oligonucleotides as indicated.

In Situ Hybridisation, Real-Time PCR, and Northern Blots

Isotopic in situ hybridisation was performed on sections of paraffin-embedded tissues and tissue microarrays (TMAs) as described previously[23] using a COP-1 specific 688 bp $^{33}$P-labeled antisense riboprobe. This probe covers most of the 5' one half of the coding sequence for COP-1 starting at nucleotide 364. A sense control probe transcribed from the same template and included in each hybridisation experiment showed no signal above background in any of the tissues. TMAs representing normal tissues and ovarian tumors were constructed as described previously[24]. The ovarian tumor TMA consists of samples of normal ovary, fallopian tube and uterus as well as 78 surface epithelial tumors. Total RNA was extracted from cells or tissue using the Qiagen RNAeasy kit and probes were designed for real-time PCR of COP1, p21, RPL19 and β-actin mRNA. All reactions were carried out according to manufacturer's recommendations using an ABI 7700 sequence detector.

Mouse Multiple Tissue Northern Blots (Clontech) were hybridized to full length, $^{32}$P-labeled murine COP1 cDNA overnight at 65° C. in Church buffer (35.5 g/L $Na_2HPO_4$, 0.17% (v/v) H3PO4, 1% (w/v) bovine serum albumin, 1 mM EDTA, 7% (w/v) SDS). Filters were washed at 65° C. in 40 mM sodium phosphate buffer pH 7.2/1% (w/v) SDS and exposed to film at −70° C.

In Vitro and In Vivo Ubiquitination Assays

For in vitro ubiquitination reactions, in vitro translated p53 was immunoprecipitated with anti-p53 (DO-1 and 1801), washed 5 times with PBST, and reactions carried out on protein A/G beads. 10 µg His-Ubiquitin (Boston Biochem) or FLAG-ubiquitin (Sigma), 20 ng of Ubc5Hb (A.G. Scientific), 20 ng rabbit E1 (Sigma), and 500 ng GST-COP1 (E3), which was preincubated with 20 µM $ZnCl_2$ for 30 minutes at room temperature, were incubated in a buffer containing 50 mM Tris pH7.5, 2 mM ATP, 5 mM $MgCl_2$, and 2 mM DTT in a total volume of 30 µl. After incubation for 2 hours at 30° C., reactions were then boiled in PBST with 1% SDS for 5 minutes and then reduced to 0.2% SDS for re-immunoprecipitation with anti-p53 (DO-1 and FL-393). Finally, samples were incubated at 95° C. in SDS sample buffer with 2-mercaptoethanol and subject to SDS-PAGE followed by immunoblotting with anti-His-HRP (Roche) or anti-FLAG-HRP (M2) to detect ubiquitinated species of p53.

For in vivo assays, H1299s or p53$^{-/-}$/MDM2$^{-/-}$ MEFs were transfected with 100 ng HA-Ub, 500 ng pcDNA3.1+ p53, 2 µg pCMV-FLAG6a, pCMV-FLAG-COP1 or pCMV-FLAG-COP1ΔRING and treated with 50 µM ALLN for 2 hours prior to harvesting and immunoprecipitation with anti-HA and western blot with anti-p53 (DO-1).

Identification of COP1-Interacting Proteins

U2-OS stable cell lines were generated expressing pCMV-FLAG-COP1 or pCMV-FLAG6a by co-transfection with pcDNA3.1+ and selecting for G418 (Invitrogen) resistance. FLAG or FLAG-COP1 expressing clones were expanded and treated with 50 µM ALLN for 2 hours before harvesting with hypotonic lysis buffer (10 mM KCl, 1.5 mM $MgCl_2$, 10 mM HEPES pH7.9, 1 mM DTT, protease inhibitor mix) followed by homogenisation. Clarified lysates by centrifugation were then subject to incubation with anti-FLAG M2 beads (Sigma). After overnight incubation, beads were washed once with wash buffer 1 (20 mM HEPES pH7.9, 420 mM NaCl, 1.5 mM $MgCl_2$, 0.2 mM EDTA, 25% Glycerol and protease inhibitor mix) and 5 times with wash buffer 2 (0.1% NP-40, 20 mM Tris pH7.5, 300 mM NaCl and protease inhibitor mix). Bound proteins were eluted with 300 µg/ml FLAG peptide (Sigma) and subsequently analysed by SDS and silver staining. Bands of interest were excised, digested with trypsin in situ, and the resulting peptides sequenced by capillary liquid chromatography-ion trap tandem mass spectrometry.

p53 Gene Sequencing, Real-Time PCR, and Western Blotting

Tumour samples were isolated and resuspended in lysis buffer (1% SDS, 20 mM Tris pH7.5, 2 mM EDTA, 400 mM NaCl) by vigorous vortexing and were supplemented with 500 µg/ml Proteinase K (Sigma) and incubated overnight at 55° C. until sample completely digested. The sample was then resuspended in a 1:1 ratio with phenol-chloroform-isoayml alcohol (25:24:1) and incubated for 30 minutes at room temperature before centrifugation at 14,000 rpm for 10 minutes. The upper aqueous layer was then resuspended in an equal volume of isopropanol and further centrifuged for 15 minutes. The resultant pellet was washed in 70% ethanol and resuspended in nuclease free $H_2O$. For the paraffin embedded tissue microarray samples, DNA was extracted by incubating microdissected tumor tissue in 30 µl PicoPure Proteinase K extraction buffer (Arcturus, Mountainview, Calif.) for 48 hours at 65° C. The digest was heat inactivated at 95° C. for 10 minutes and added directly to PCR reactions (Expand High Fidelity PCR system, Roche Molecular Biochemicals, Indianapolis, Ind.). Isolated genomic DNA was subject to PCR with the following primers for exons 5-8 of the p53 gene incorporating M13-specific sequences:

```
                                        (SEQ ID NO: 11)
Exon 5R  (CAGGAAACAGCTATGACCAGCCCTGTCGTCTGTCCA)

(SEQ ID NO: 12)
Exon 5F  (TGTAAAACGACGGCCAGTTTCAACTCTGTCTCCTTC)

(SEQ ID NO: 13)
Exon 6R  (CAGGAAACAGCTATGACCTTAACCCCTCCTCCCAGAGA)
```

-continued

```
                                        (SEQ ID NO: 14)
Exon 6F  (TGTAAAACGACGGCCAGTGCCTCTGATTCCTCACTGAT)

(SEQ ID NO: 15)
Exon 7R  (CAGGAAACAGCTATGACCTGTGCAGGGTGGCAAGTGGC)

(SEQ ID NO: 16)
Exon 7F  (TGTAAAACGACGGCCAGTAGGCGCACTGGCCTCATCTT)

(SEQ ID NO: 17)
Exon 8R  (CAGGAAACAGCTATGACCAGGCATAACTGCACCCTTGG)

(SEQ ID NO: 18)
Exon 8F  (TGTAAAACGACGGCCAGTCCTTACTGCCTCTTGCTTCTC).
```

PCR products were sequenced using fluorescent dye-terminator chemistry (Applied Biosystems, Foster City Calif.) with M13F and M13R sequencing primers.

Real-time PCR was carried out with specific probes for COP1, p21, Pirh2, b-actin and RPL19 as follows, from total RNA isolated from normal and tumour samples. All reactions were carried out according to manufacturer's recommendations using an ABI 7700 sequence detector.

RT-PCR Primer Sequences: (All Primers Amplify a Segment of the 3'UTR for Each Gene)

```
ss.Pirh2-1290F -
TCCTCTAAATGTGAATTTTGATGTAA           (SEQ ID NO: 19)

ss.Pirh2-1463R -
TCCCAACTACTTTTATGGAATACCT            (SEQ ID NO: 20)

ss.Pirh2-1359T -
TTTTCCAAAGTTTTCTATGTTTGGCTCAATTAGG   (SEQ ID NO: 21)

p21WAF1-1866F -
GTGCTTAGTGTACTTGGAGTATTGG            (SEQ ID NO: 22)

p21WAF1-1939R -
AGTCCAGGCCAGTATGTTACAG               (SEQ ID NO: 23)

p21WAF1-1893T -
TCTGACCCCAAACACCTTCCAGC              (SEQ ID NO: 24)

b-actin-1312F -
AAAACTGGAACGGTGAAGGT                 (SEQ ID NO: 25)

b-actin-1380R -
CGGCCACATTGTGAACTT                   (SEQ ID NO: 26)

b-actin-1356T -
ATGCTCGCTCCAACCGACTGC                (SEQ ID NO: 27)

hCOP-2362F -
CCTTTGGGACATTGGGAAT                  (SEQ ID NO: 28)

hCOP-2436R -
CCACCAAGAGCAGCAATGT                  (SEQ ID NO: 29)

hCOP-2382T -
CCCAGCCAACTCTCCACCATCAA              (SEQ ID NO: 30)

RPL19 sequences:
DNA103410-432F
AGCGGATTCTCATGGAACA                  (SEQ ID NO: 31)

DNA103410-502R
CTGGTCAGCCAGGAGCTT                   (SEQ ID NO: 32)

DNA103410-453T
TCCACAAGCTGAAGGCAGACAAGG             (SEQ ID NO: 33)
```

Tissues were harvested in TLB (0.5% NP40, 20 mM Tris pH7.5, 5 mM EDTA, protease inhibitor mix (Roche)) followed by homogenisation. Lysates were cleared by centrifugation at 20,000×g for 60 minutes before being subject to SDS-PAGE and western blot analysis. Membranes were probed with antibodies to COP1, p53 (DO-1 and 1801, Santa Cruz Biotechnology), and actin (ICN).

Immunohistochemistry for COP1 and p53

Tissues were collected and fixed in 10% neutral buffered formalin and embedded in paraffin. 5µ sections on glass slides were deparaffinized and hydrated in distilled water. For p53 staining, slides were incubated for 20 minutes in Dako Target Retrieval (Dako, S1700) solution at 99° C., slides were then rinsed in TBST. Endogenous peroxidase, avidin and biotin were quenched using KPL blocking buffer (KPL, 37-00-84) and Vector avidin/biotin kit (Vector, SP2001) respectively, followed by TBST rinses. Slides were incubated for 30 minutes in 10% normal horse serum in 3% BSA/PBS. Slides were then incubated in 5 µg/ml anti-p53 antibody (Novus Biologicals, NB200-104) for 60 minutes at room temperature. After washes in TBST, slides were incubated with 2.5 µg/ml biotinylated horse anti-mouse secondary antibody (Vector, BA2001) for 30 minutes at room temperature. Following TBST washes slides were incubated with Vectastain ABC Elite Reagents (Vector, PK6100) for 30 minutes at room temperature. Slides were then rinsed with TBST, incubated with Pierce Metal Enhanced DAB for four minutes, and rinsed in water. Slides were then counterstained with Mayer's hematoxylin, dehydrated, mounted and coverslipped for bright field viewing. For COP1 staining, slides were incubated for 20 minutes in Dako Target Retrieval High pH solution (Dako, S3308) at 99° C., slides were then rinsed in TBST. Endogenous peroxidase, avidin and biotin were quenched using KPL blocking buffer and Vector avidin/biotin kit followed by TBST rinses. Slides were incubated for 30 minutes in 10% normal horse serum in 3% BSA/PBS. Slides were then incubated in 1 µg/ml anti-COP1 (clone 1D5) antibody for 60 minutes at room temperature. After washes in TBST, slides were incubated with 2.5 µg/ml biotinylated horse anti-mouse secondary antibody for 30 minutes at room temperature. Following TBST washes slides were incubated with Vectastain ABC Elite Reagents for 30 minutes at room temperature. Slides were then incubated in biotinyl tyramide reagent (Perkin Elmer, NEL700) for 3 minutes followed by TBST wash and then incubation with Vectastain ABC Elite Reagents for 30 minutes. Following TBST washes slides were incubated with Pierce Metal Enhanced DAB for four minutes, and rinsed in water, counterstained with Mayer's hematoxylin, dehydrated, mounted and coverslipped.

Example 2 p53 is a Substrate for COP1

To gain an understanding of how COP1 may be modulating cellular processes, lysates from U2-OS cells stably expressing FLAG-tagged COP1 or empty vector were subject to immunoprecipitation with anti-FLAG and bound proteins were eluted via FLAG peptide and analysed by SDS-PAGE with specific bands sequenced by mass spectrometry (FIG. 1A). Mass spectrometry analysis of a band at approximately 53 kDa revealed 5 matching peptides from the tumour suppressor protein p53. To confirm that this interaction is bona fide, p53-null Soas-2 cells were transfected with p53 and Myc-COP1, immunoprecipitated with anti-p53 (DO-1) and immunoblotted with anti-Myc (FIG. 1B). COP1 was only immunoprecipitated in the presence of transfected p53, thereby indicating that COP1 can interact with p53. This interaction was also seen with transfected COP1 and endogenous p53 (FIG. 1C). In addition, there was an interaction between p53 and COP1 at the endogenous protein level in U2-OS cells (FIG. 1D). And in vitro-translated haemagglutinin (HA)-COP1 was able to interact with glutathione S-transferase (GST)-p53 in vitro (FIG. 1E).

Figure 2:
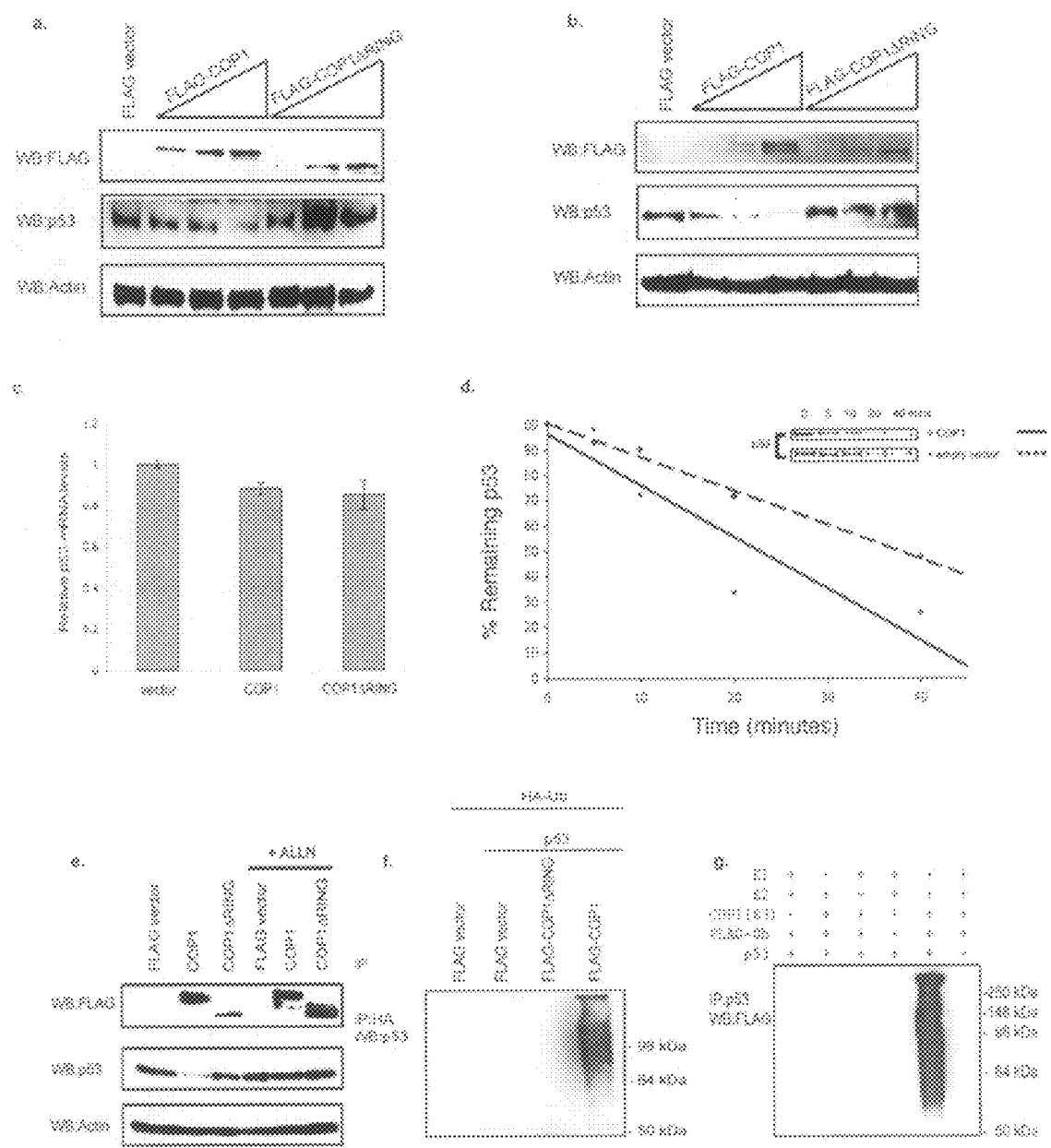
FIGS. 2A-I. COP1 negatively regulates p53 expression and transactivation activity and maintains the ability to degrade p53 in the absence of MDM2 or Pirh2. A, COP1 hinders the steady-state level of exogenous p53 protein. COP1 or COP1☐RING was transfected with p53 into Saos-2 (p53-null) cells, and steady-state levels of p53 were assessed by immunoblotting. B, COP1 hinders steady-state levels of endogenous p53 protein. COP1 or COP1☐RING was transfected into U2-OS cells and steady-state levels of endogenous p53 were assessed by immunoblotting. C, COP1 does not alter p53 mRNA levels. RNA from U2-OS cells transfected with COP1 or COP1ΔRING was extracted, and p53 mRNA levels were assessed by real-time PCR and normalized to beta-actin mRNA. D, COP1 increases p53 turnover. HEK293T cells were transfected with or without COP1, and the half-life of endogenous p53 was determined by pulse-chase metabolic labelling. E, COP1 degradation of p53 requires a functional 26S proteasome. U2-OS cells were transfected as in B, except that cells were treated with or without the proteasome inhibitor ALLN for 6 h before collecting lysates. F, COP1 promotes ubiquitination of p53 in vivo. Saos-2 cells were transfected with HA-ubiquitin, p53 and COP1 or COP1ΔRING, and treated with ALLN. Ubiquitinated p53 was detected by immunoprecipitation with anti-HA and immunoblotting with anti-p53. G, COP1 directly ubiquitinates p53 in vitro. Bacterially expressed and purified ubiquitin components were incubated with in vitro-translated and immunoprecipitated p53 as indicated. Ubiquitinated p53 was detected with anti-Flag and is represented as products >53 kDa. H, COP1 dampens the transactivation function of p53 on the p21 promoter. Saos-2 cells were transfected with p53 and COP1 or COP1ΔRING with a p21-Luc reporter and internal control pCMV-b-Gal plasmid. RLU, relative light units. I, COP1 prohibits p53-dependent apoptosis. Saos-2 cells were transfected with p53 and COP1 as indicated. Transiently transfected cells were selected by co-transfection of EGFP, and the resultant sub-G1 population was assessed by propidium iodide staining for cell-death estimation. J, COP1 promotes p53 degradation in an MDM2-independent manner. MEFs derived from p53/MDM2 null mice were transfected with constructs as indicated and lysates were subject to immunoblotting with antibodies to p53, actin, MDM2, and FLAG. K, COP1 promotes p53 degradation in a Pirh2-independent fashion. Saos-2 cells were depleted of Pirh2 by siRNA and subsequently transfected with p53 and FLAG-COP1, or MDM2. Effects on steady-state levels of p53 were assessed by immunoblotting. Pirh2 mRNA ablation was confirmed by real-time PCR. L, COP1 inhibits p53-dependent transcription from bax promoter. Saos-2 cells were transfected with p53 and FLAG-COP1 or FLAG-COP1ΔRING incorporating the reporter bax-Luc and internal control pCMV-βGal. Relative transactivation activity was assessed by normalising luciferase to β-Gal activity. M, COP1 inhibits transactivation activity of endogenous p53. U2-OS cells were transfected with pG13-Luc or NS-Luc, and pCMVβ-Gal with an increasing quantity of FLAG-COP1 or FLAG-COP1ΔRING. After 24 hours of transfection, cells were treated with 10 µM etoposide or DMSO and luciferase activity determined 6 hours after treatment.
Figure 2:
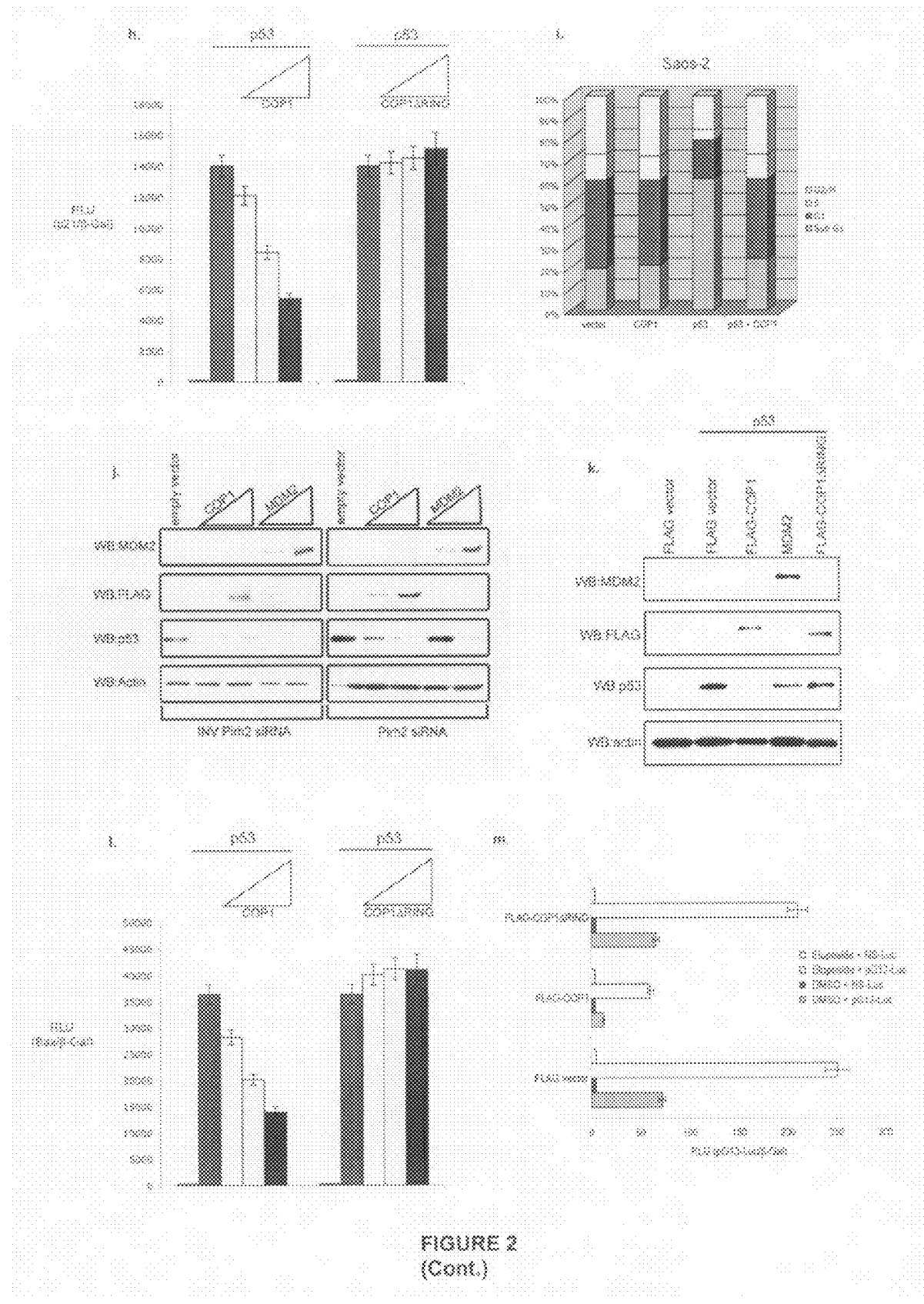

The potential for COP1 to affect the steady-state levels of p53 protein was assessed by transfecting a constant amount of p53 with increasing amounts of FLAG-COP1 or a mutant of COP1 lacking the RING finger domain, FLAG-COP1ΔRING. Transfection of COP1 resulted in a reduction in the steady-state levels of exogenous p53 protein, which was abrogated upon deletion of the RING finger domain (FIG. 2A). To assess whether COP1 affects the steady-state level of endogenous p53, U2-OS cells were transfected with FLAG-COP1 or FLAG-COP1ΔRING (FIG. 2B). As in the case of exogenous p53, COP1 was able to decrease the steady-state levels of endogenous p53, which was dependent upon the RING finger domain of COP1.

To gain further insight into the mechanism of this reduction in p53 protein levels, real-time PCR was carried out on the p53 gene to determine whether COP1 inhibited p53 gene transcription (FIG. 2C). Transfection of Flag-COP1 or Flag-COP1ΔRING in U2-OS cells resulted in no significant change in p53 messenger RNA levels. However, using pulse-chase analysis, transfection of COP1 in human embryonic kidney HEK293T cells showed a clear reduction in the half-life of p53 relative to the empty vector control, indicating that COP1 actively increases the turnover of p53. Given that the half-life of p53 is considerably shortened by COP1 overexpression, and that this is independent of p53 mRNA effects or any direct effect on MDM2 protein levels, this effect may be post-translational.

To test this hypothesis, U2-OS cells were transfected with FLAG-COP1 or FLAG-COP1ΔRING and treated with DMSO or the proteasome inhibitor ALLN (FIG. 2E). The addition of ALLN markedly increased the level of p53 protein, which was previously reduced by transfection of Flag-COP1, indicating that COP1 directs p53 for proteasome-mediated degradation.

To determine if COP1-mediated degradation of p53 via the proteasome is a consequence of p53 ubiquitination, H1299 or Saos-2 cells were transfected with p53, FLAG-COP1 or FLAG-COP1ΔRING, and HA-Ubiquitin (FIG. 2F). Immunoprecipitation with anti-HA and immunoblotting with anti-p53 revealed the presence of ubiquitinated species of p53 only with co-transfection of FLAG-COP1. These data suggest that COP1 targets p53 for degradation via the proteasome by ubiquitination.

To ascertain whether COP1 acts through MDM2 or Pirh2 to modulate p53 degradation, transient transfections with p53 and COP1 or COP1ΔRING were carried out in p53$^{-/-}$/MDM2$^{-/-}$ mouse embryo fibroblasts (MEFs), or in Saos-2 cells depleted of Pirh2 by siRNA, and their ability to affect p53 steady-state levels was assessed (FIGS. 2J, K). Essentially, COP1 was able to recapitulate the negative regulation of p53 achieved in MDM2- and Pirh2-containing cells. These results imply that COP1 can function independently of MDM2 at regulating p53.

Since COP1 modulates the ubiquitination of p53 in vivo (FIG. 2F) we wished to determine if p53 is a direct substrate for COP1 in vitro. GST and GST-COP1 were expressed in *E. coli*, purified, and subsequently used for ubiquitination assays with in vitro translated p53 (FIG. 2G). Only with all of the reaction components and p53 present was COP1 able to directly ubiquitinate p53. Therefore, these data indicate that COP1 serves as an E3-ligase for p53.

Example 3

To determine the effect of COP1 overexpression on p53-dependent transactivation, Saos-2 cells were transfected with p53 and COP1 or COP1ΔRING, and p21-luciferase (Luc) or bax-Luc (FIGS. 2H, L). The addition of COP1 markedly reduced the ability of p53 to transactivate from the p21 and bax promoter. Moreover, the transactivation ability of endogenous p53, as well as that induced by DNA damage, was in the same manner abrogated by the overexpression of COP1 (FIG. 2M). To assess further the ability of COP1 to negatively regulate p53, we ascertained whether COP1 could inhibit p53-induced cell death in Saos-2 cells (FIG. 2I). Transfection of p53 markedly increased the population of cells in the SubG1 population; nevertheless, this was strikingly prohibited by the co-transfection of COP1, suggesting that COP1 inhibits p53-induced cell death. Transfection of COP1 alone had no profound effect on cell cycle distribution.

Figure 3:
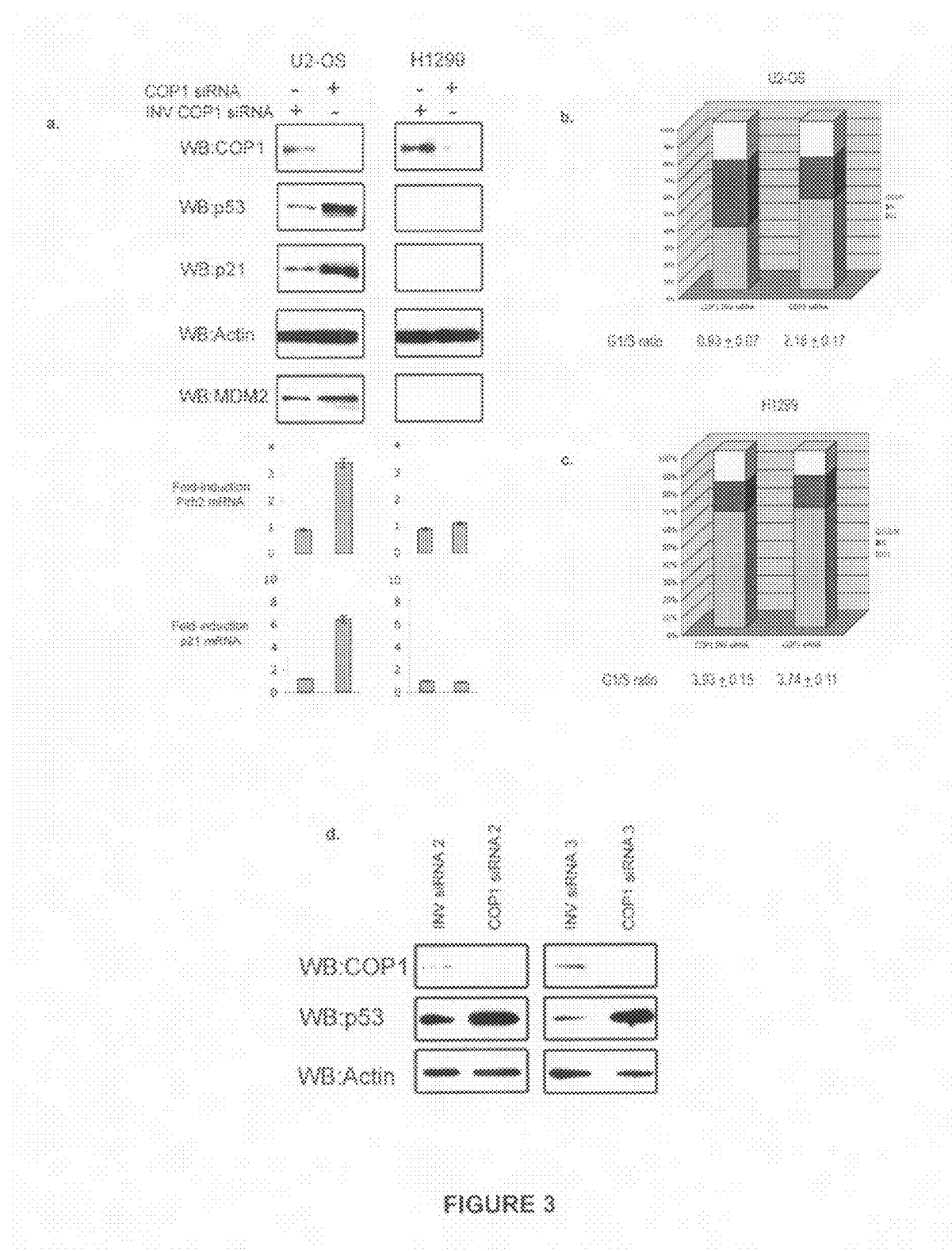
FIGS. 3A-D. siRNA ablation of COP1 causes an accumulation of p53 protein and induces a G1 arrest. A, siRNA ablation of COP1 increases the steady-state level of p53 protein and increases transactivation of the p21 and Pirh2 genes. U2-OS and H1299 cells were transfected with siRNA oligonucleotides to COP1 or COP1 inverted as a control. Lysates were immunoblotted with the indicated antibodies and mRNA of target genes was detected by real-time PCR. B, C, siRNA ablation of COP1 induces a G1 arrest that is p53-dependent. U2-OS (B) or H1299 (C) cells were transfected with COP1 or inverted COP1 siRNA oligonucleotides, and cell-cycle profile was determined by propidium iodide staining and FACS. D, Ablation of COP1 by two further distinct siRNA oligos causes an accumulation of p53 at the protein level. U2-OS cells were transfected with either COP1 siRNA2 or COP1 siRNA3 and lysates.

To uncover the role of COP1 in a more physiological setting, endogenous COP1 was subject to ablation by siRNA, and any effect on endogenous p53 steady-state levels was assessed (FIG. 3A). Knockdown of COP1 was assessed by real-time PCR and immunoblotting. Depletion of COP1 by siRNA in U2-OS cells caused a pronounced accumulation of p53 protein. These results were reproducible with two further independent siRNA oligonucleotides (FIG. 3D), indicating that COP1 negatively regulates p53 in unstressed cells. With such a dramatic accumulation of p53 protein levels, we next ascertained whether p53 could induce its downstream target genes, p21 and Pirh2. Using real-time PCR, we observed a pronounced increase in p21 and Pirh2 mRNA in response to COP1 ablation, indicating an increase in p53-dependent transcription. Furthermore, total p21 protein levels were dramatically increased by the introduction of COP1 siRNA. In contrast, the transfection of COP1 siRNA oligonucleotides into the p53-null cell line H1299 had no effect on p21 protein or on p21 and Pirh2 mRNA levels. Furthermore, depletion of COP1 in U2-OS cells caused a prominent increase in the G1/S ratio (1.82 to 3.71), but failed to have any effect in the H1299 cells (FIG. 3C), indicating that a G1 arrest occurred in a p53-dependent manner.

Figure 4:
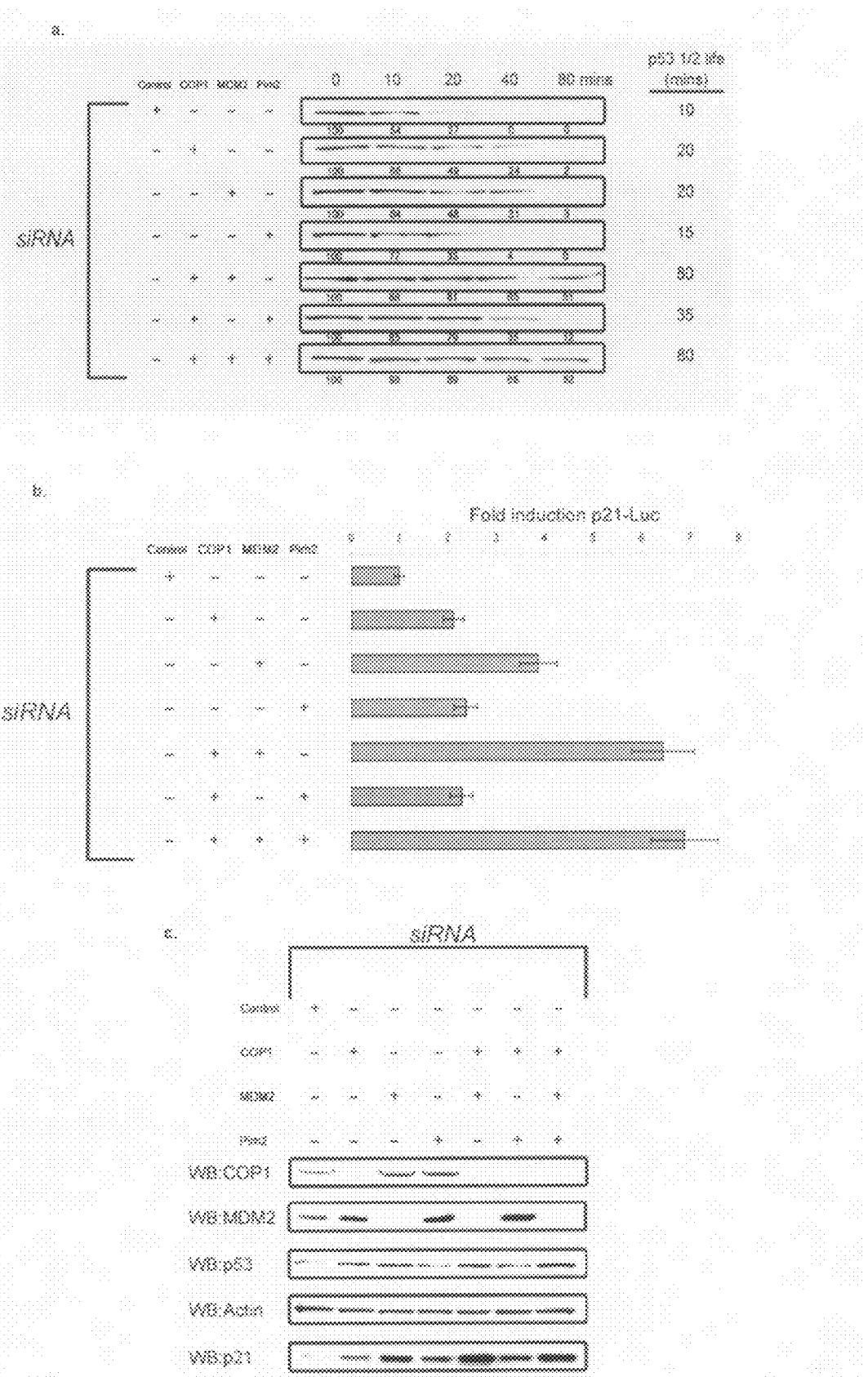
FIGS. 4A-E. COP1, Pirh2 and MDM2 ablation by siRNA stabilizes and activates p53. A, Ablation of COP1 stabilizes p53. U2-OS cells were transfected with siRNA oligonucleotides to COP1, MDM2 and/or Pirh2, and subsequently pulse-chased for the indicated period of time. Lysates were then harvested and immunoprecipitated with antip53 and quantified on a phosphorimager. B, The transactivation activity of p53 is increased upon diminishment of COP1. U2-OS cells were transfected with the indicated siRNA oligonucleotides and p21-Luc reporter, and relative transactivation activity was determined by normalizing luciferase to an internal transfection control, pCMV-beta-Gal activity. C, p53 and the downstream target p21 accumulate at the protein level in response to ablation of COP1 and are further stimulated by co-ablation of MDM2. Lysates from b were probed with antibodies to p53, p21, COP1 and MDM2. D, COP1 negatively regulates p53 in normal cells. BJ fibroblasts were transfected with siRNA oligonucleotides as in C, and lysates were harvested and immunoblotted with antibodies to p53, p21, actin, MDM2 and COP1. E, Ablation of COP1 and MDM2 by siRNA sensitizes U2-OS cells to IR-induced cell death. U2-OS cells were pre-treated with siRNA oligonucleotides as indicated, and subjected to 20 Gy IR and cell death determined by propidium iodide staining.
Figure 4:
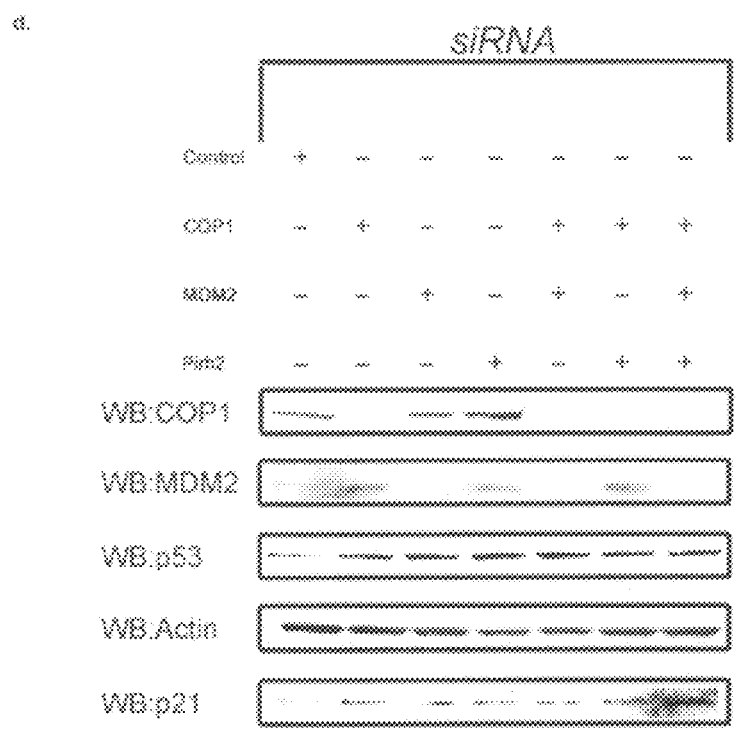
Figure 4:
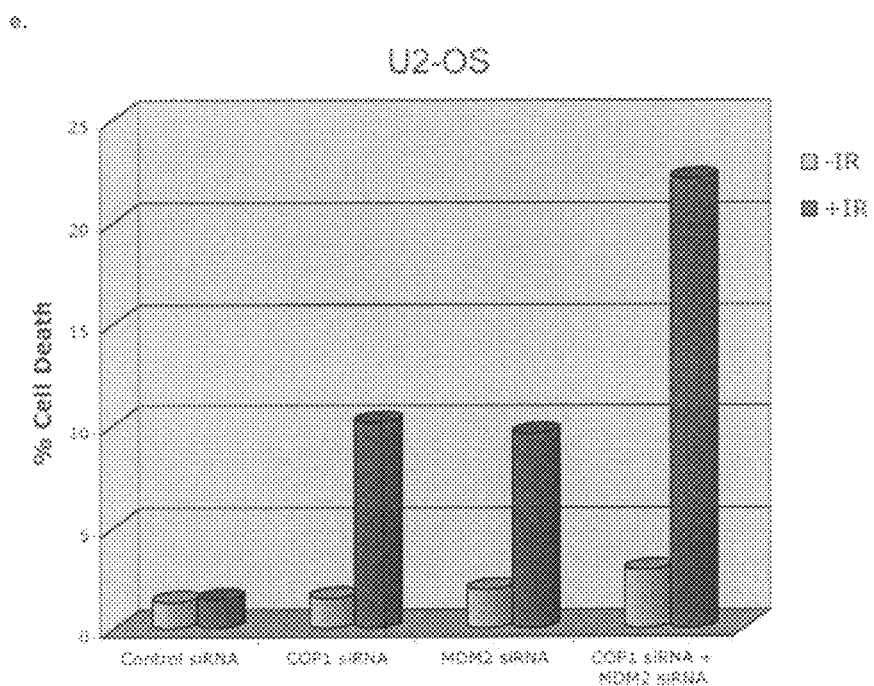

To confirm that COP1 mediates p53 turnover in unstressed cells, pulse-chase analysis was carried out in U2-OS cells depleted of COP1 (FIG. 4A). Ablation of COP1 protein increased the half-life of p53 2-fold relative to control. Pirh2 and MDM2 were also ablated by siRNA for pulse-chase analysis and comparison with COP1. Depletion of Pirh2 increased the half-life of p53 1.5-fold, whereas MDM2 ablation increased the half-life of p53 2-fold over control. To place COP1 in the context of MDM2 and Pirh2, co-ablation of COP1 and Pirh2 by siRNA resulted in a further enhancement of p53 half-life, 3.5-fold over control. Surprisingly, ablation of COP1 and MDM2 together resulted in a synergistic 8-fold increase in p53 halflife. This was not further enhanced by simultaneous Pirh2 depletion, suggesting that the half-life of p53 had reached a maximum in this particular system. Reporter assays were carried out to measure the transactivation function of p53 (FIG. 4B). Consistent with an increase in the half-life of p53, there was a modest increase in transactivation from the p21 promoter upon ablation of COP1, Pirh2 or MDM2, with the highest stimulation derived from ablation of MDM2. These observations were also confirmed at the protein level (FIG. 4C). There was also a pronounced stimulation from the p21 promoter and an increase in protein levels in response to co-ablation of COP1 and MDM2 (FIGS. 4A, B). It is noteworthy that in response to ablation of all E3 ligases, there was no further enhancement of p53 or p21 protein levels (FIG. 4C), or of promoter activity (FIG. 4B), suggesting that proliferating cells may have a limited threshold for p21 and/or p53. Furthermore, ablation of COP1, Pirh2 or MDM2 resulted in an increase in p53 and p21 steady-state levels in normal BJ fibroblasts, indicating that each ligase has a role in negatively regulating p53 in normal cells (FIG. 4D).

With the observations that ablation of COP1 and MDM2 resulted in a p53 response, we tested whether depletion of COP1 and/or MDM2 would restore a normal DNA-damage response in U2-OS cells, because they are known to be highly resistant to ionizing radiation (IR)-induced cell death[31]. U2-OS cells were transfected with siRNA oligonucleotides to COP1 and/or MDM2, and subsequently treated with 20 Gy IR, and cell death was assessed by propidium iodide staining (FIG. 4E). U2-OS cells pre-treated with control siRNA were highly resistant to cell death after treatment with IR; however, cells pre-treated with COP1 or MDM2 siRNA resulted in a subpopulation of cells that were sensitive to IR-induced cell death. More strikingly, simultaneous ablation of COP1 and MDM2 by siRNA resulted in a cooperative sensitization to cell death by IR.

COP1 is a p53-Inducible Gene that Participates in a Negative Feedback Loop

Figure 5:
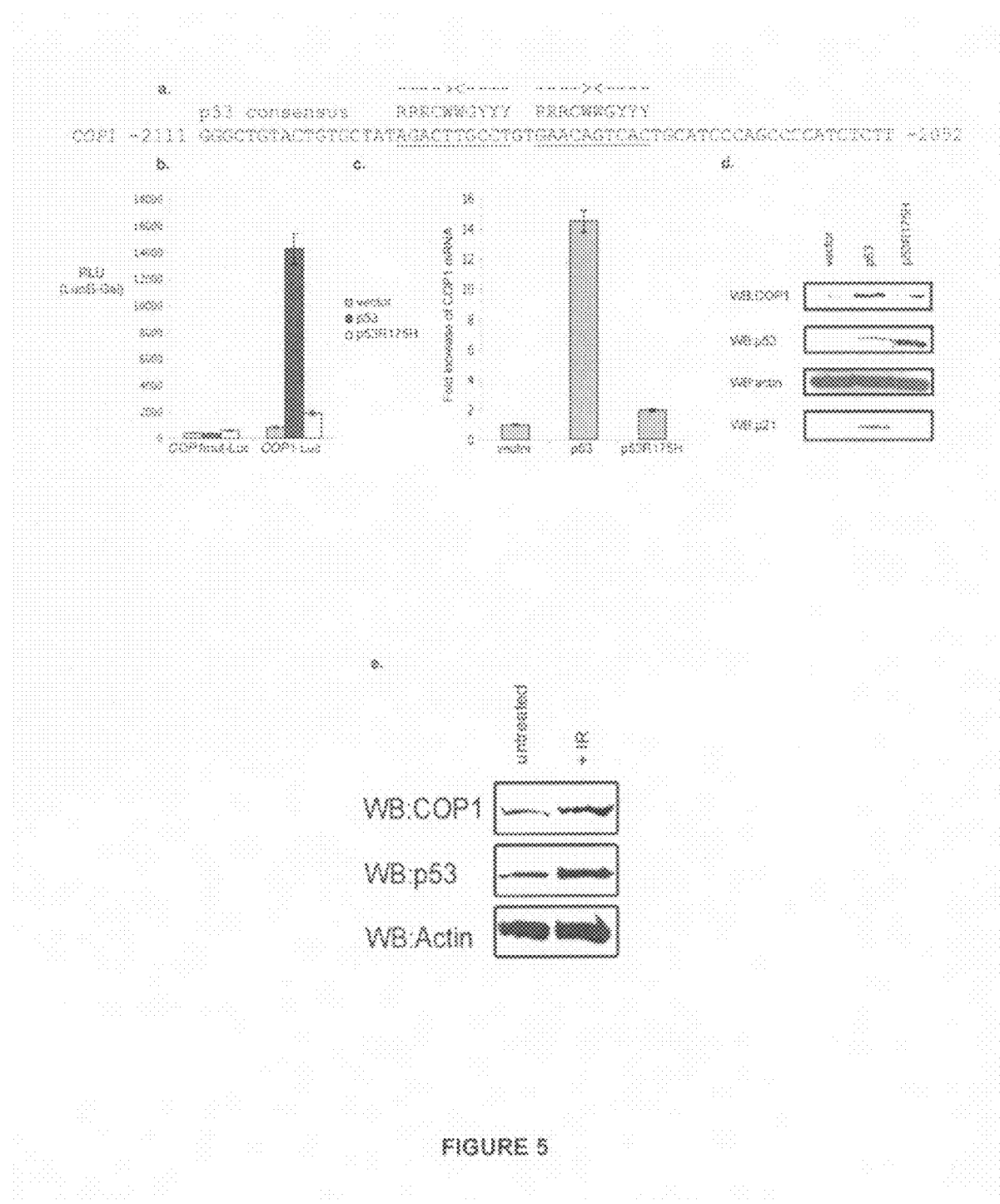
FIGS. 5A-E. COP1 is a p53-inducible gene. A, Identification of a p53 consensus site on the COP1 promoter. Underlined sequence represents a p53 decamer. B, The p53 consensus site from COP1 promoter is able to stage p53-dependent transcription. Two copies of the COP1 consensus site for p53 were introduced upstream of the pGL3-Promoter luciferase reporter construct and co-transfected with wild-type p53 or mutant p53 R175H. Relative activity was determined by normalizing to pCMV-beta-Gal activity. C, COP1 mRNA is induced by p53. H1299 cells were transfected with p53 or R175H mutant, and RNA was isolated and subjected to real-time PCR using a probe specific for COP1 mRNA and normalized tob-actin mRNA. D, COP1 protein levels are increased by p53. Lysates from C were immunoblotted with antibodies to p53, p21, actin and COP1. E, COP1 protein levels are increased in response to IR. U2-OS cells were irradiated with 10 Gy IR and harvested after 8 h. Lysates were immunoblotted with antibodies to p53, actin and COP1.

Given that MDM2 and Pirh2 form an autoregulatory feedback loop, we investigated the possibility that COP1 may also be part of such a regulatory mechanism. Scanning the promoter region of the COP1 gene revealed the presence of a p53 consensus-binding site 32 from −2094 to −2073 relative to the transcriptional start site (+1) (FIG. 5A). Two copies of this consensus site (COP1-Luc) or mutants of this consensus version (COP1mut-Luc) were inserted upstream of a luciferase reporter gene containing a minimal promoter, and transfected into H1299 cells with pcDNA3.1+, p53 or the DNA-binding mutant, p53R175H (FIG. 5B). Transfection of p53 increased the luciferase activity of COP1-Luc, but not the COP1mut-Luc reporter construct, whereas the p53R175H mutant failed to have any profound effect on COP1-Luc or COP1mut-Luc. Furthermore, transfection of p53 substantially increased COP1 mRNA levels within H1299 cells, as assessed by real-time PCR (FIG. 5C). An increase in total COP1 protein was also detected by western blot with anti-COP1 (FIG. 5D). In addition, U2-OS cells treated with IR, which activates p53-dependent transcription and stabilizes p53, resulted in an increase in COP1 protein levels (FIG. 5E) relative to untreated cells. As controls, p21 and p53 protein levels were also assessed by immunoblotting to verify that the IR insult elicited a p53 response. Taken together, these data suggest that COP1 is a p53-inducible gene that participates in a negative feedback loop.

COP1 is Overexpressed in Cancer Cells

Figure 6:
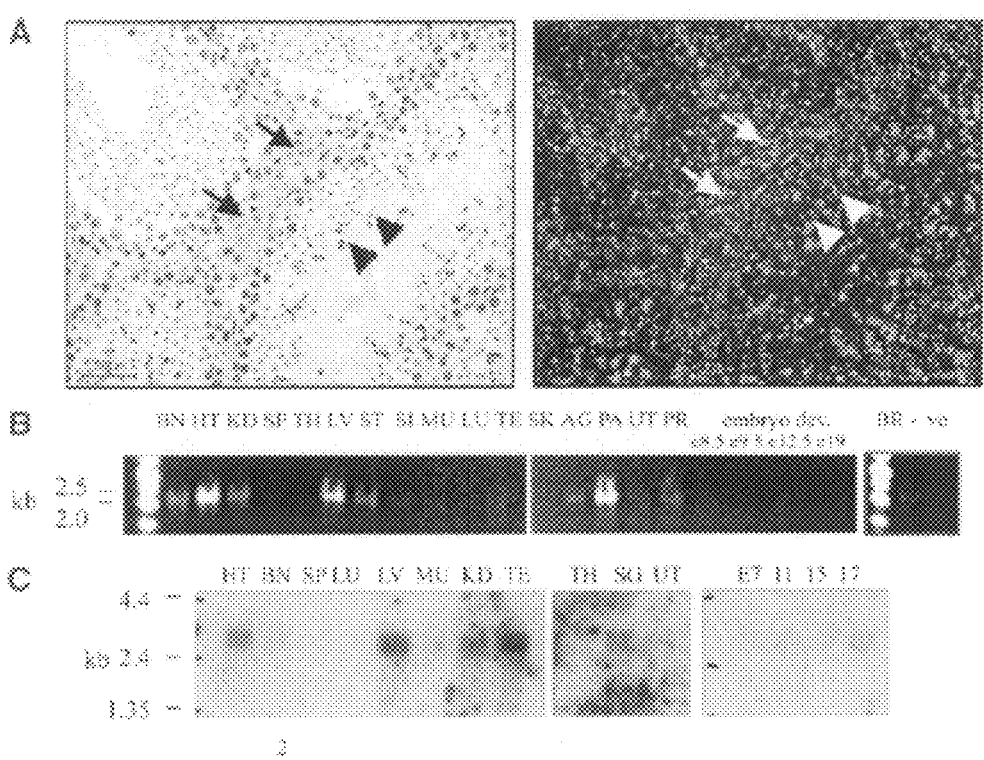
FIGS. 6A-C. COP1 expression in murine tissues. A: ISH analysis of COP1 in normal testes. Left panel represents bright-field and right panel dark-field. B: RT-PCR of full-length COP1 using a 1st Strand cDNA panel. C: Northern blot analysis of full-length COP1 expression.

COP1 expression was examined in mammalian cells/tissues by real-time PCR and in situ hybridisation (ISH) techniques. We performed expression analysis in normal murine tissues by ISH (FIG. 6A), RT-PCR (FIG. 6B), and Northern blot (FIG. 6C). ISH analyses demonstrated that cop1 was expressed in normal murine skeletal muscle, intestines, and testes. In the testes, prominent expression was evident in the Leydig cells although moderate signal was also present in the germ cells (FIG. 6A). The Northern blot panel confirmed that cop1 was expressed in the testes as well as the heart, liver, and kidneys (FIG. 6C). The cDNA panel RT-PCR also demonstrated that cop1 was expressed in brain, stomach, small intestine, pancreas, adrenal gland, uterus, and prostate. The RT-PCR and Northern blot panels were in good agreement for the tissue distribution of the full-length cop1 mRNA expression. In addition to murine tissues, we evaluated human tissue by ISH and identified cop1 expression in normal human tonsil, spleen, testes, pancreas, and colon. This is consistent with previous findings showing prominent cop1 expression by Northern blot in normal human testes, thymus, colon, heart, prostate, spleen, intestine, and liver.[36]

Figure 7:
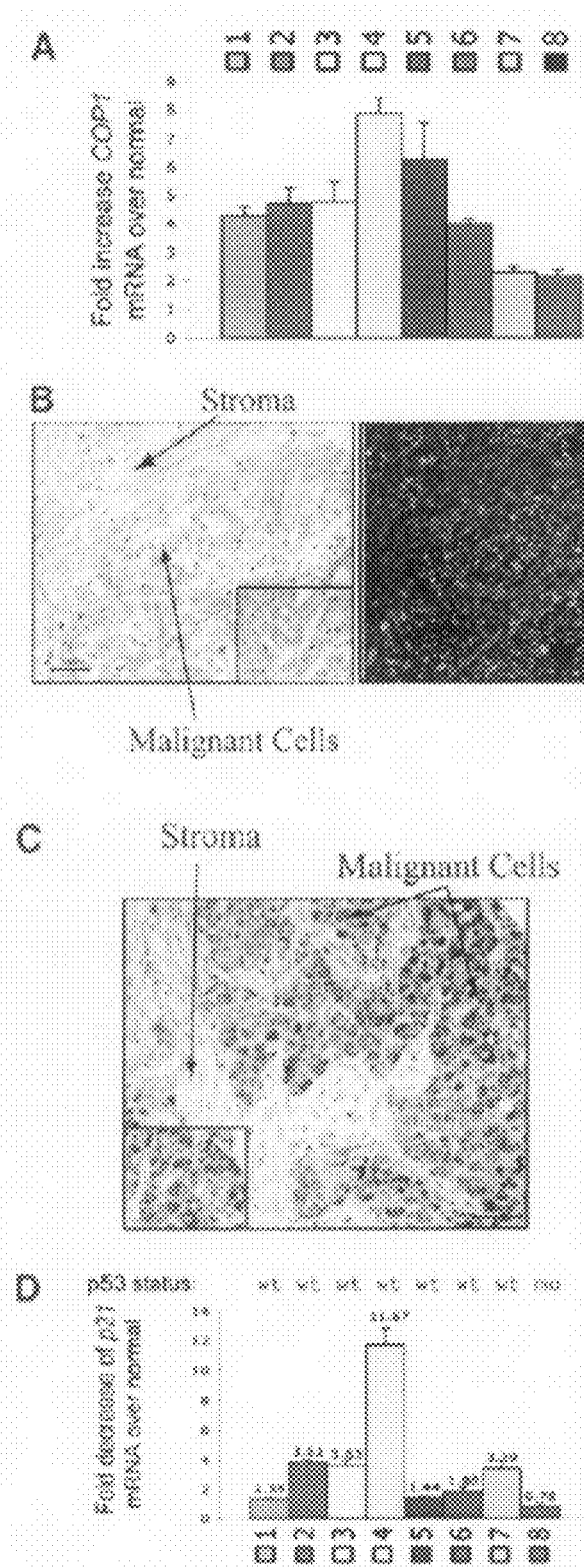
FIGS. 7A-D. COP1 overexpression in ovarian adenocarcinomas. A: Real-time PCR analysis of cop1 mRNA from ovarian tumours. RNA was prepared from tumour samples with matched normal controls and subject to real-time PCR Taqman analysis. Data are represented as fold increase over matched normal cop1 mRNA and were normalised to RPL19 mRNA. B: Overexpression of cop1 mRNA by ISH. cop1 expression was evident in neoplastic epithelial cells but not associated stroma; normal ovarian tissue was negative. C: Overexpression of COP1 at the protein level in ovarian adenocarcinomas. The same case of ovarian adenocarcinoma as in B demonstrates COP1 immunoreactivity in the cytoplasm and nucleus of neoplastic epithelial cells but not associated stroma. D: p53 gene status in ovarian tumours and correlation of COP1 overexpression with decrease in p21 mRNA. DNA was extracted from the samples in A and subject to PCR of exons 5-8 of the p53 gene with the products being analysed by DNA sequencing and designated as wild-type (wt) or mutant (mu). The graph below the p53 gene status shows the same samples from A that overexpressed COP1 also had decreased p21 mRNA. The relative levels of p21 mRNA were determined by real-time PCR as in A and normalised to RPL19 mRNA. Data are represented as fold decrease in p21 message.

To determine if COP1 gene expression was altered in cancers, total RNA was harvested from various normal and tumour samples and relative cop1 expression was determined by real-time PCR and normalising to RPL19 mRNA. There was a significant increase of 2-8 fold in cop1 mRNA over normal controls (FIG. 7A). We therefore carried out a larger scale study using a cop1 specific probe for ISH on an ovarian tissue microarray (TMA) comprised of 0.6 mm cores of 67 ovarian adenocarcinoma cases in triplicate. 30% (8/27) cases of serous adenocarcinoma displayed a positive signal only within the malignant cells, whereas no signal was observed within the stromal compartment (FIG. 7B) or normal ovarian tissues. Moreover, 16% (3/19) cases of endometrioid adenocarcinoma and 27% (3/11) cases of clear cell adenocarcinoma displayed a positive signal for mRNA encoding COP1 (Table 1).

TABLE 1

Summary of ovarian adenocarcinoma cases on the tissue microarray. COP1 expression was demonstrated by ISH and IHC.

| Core Diagnosis | ISH (#positive/total cases) | IHC (#positive/total cases) |
| --- | --- | --- |
| Serous adenocarcinoma | 8/27 | 11/27 |
| Endometrioid adenocarcinoma | 3/19 | 12/19 |
| Clear cell adenocarcinoma | 3/11 | 4/11 |
| Mucinous adenocarcinoma | 0/10 | 5/10 |
| Total cases of ovarian adenocarcinoma | 14/67 | 32/67 |

To confirm that COP1 is overexpressed in these tumours at the protein level, IHC analysis using a specific antibody to COP1 was done on the same ovarian TMA described above as well as the ovarian samples used for RT-PCR in FIG. 7A. Results for the TMA are summarized in Table 1 showed 47% (11/27) of serous adenocarcinomas, 63% (12/19) of endometrioid adenocarcinomas, 36% (4/11) of clear cell adenocarcinomas, and 50% (5/10) of mucinous adenocarcinomas displayed a robust COP1 immunoreactivity within the nuclear and cytoplasmic compartments of the malignant cells; however, no signal was detected within the stroma (FIG. 7C). In addition, normal tissues were negative for any reactivity with the COP1 antibody. Collectively, these data indicate that COP1 mRNA and protein are specifically overexpressed in the malignant cells. There was good agreement with the ISH and IHC data (Table 1); endometrioid and mucinous adenocarcinomas displayed a higher percentage of COP1 positive samples by IHC, relative to the ISH data, suggesting post-transcriptional regulation of COP1.

Next we wished to determine if any of the tumour samples that overexpress COP1 harboured a defect in a p53-dependent response. To address this question we carried out real-time PCR on the ovarian tumours that overexpressed COP1 (FIG. 7A) using specific probes to the p53 target gene and cyclin-dependent kinase inhibitor, p21/WAF1, with fold-change in mRNA assessed by comparing to normal control samples. The majority of the samples that overexpressed COP1 showed a significant decrease in p21 mRNA over matched normal controls (FIG. 7D). These results are consistent with COP1 negatively regulating p53's ability to activate transcription of p21.

Given that p53 can be mutated in ovarian cancers it is important to determine the p53 gene status in these samples since specific mutants of p53 lose their inherent ability to transactivate from the p21 promoter. For example, if p53 is mutated in the samples where COP1 is overexpressed then the downregulation of p21 mRNA observed might be independent of p53. Therefore, we sequenced exons 5-8, as well as the intron-exon boundaries, where p53 mutation is frequently identified and found 7/8 of these samples were wild-type and 1/8 had the R249S mutation, which is located in the p53 DNA binding region and has been shown to immortalise normal mammary epithelial cells.[37] Moreover, the R249S mutant ovarian sample (number 8) had normal levels of p21 mRNA, consistent with the repression of wild-type p53-dependent transcription by COP1.

Figure 8:
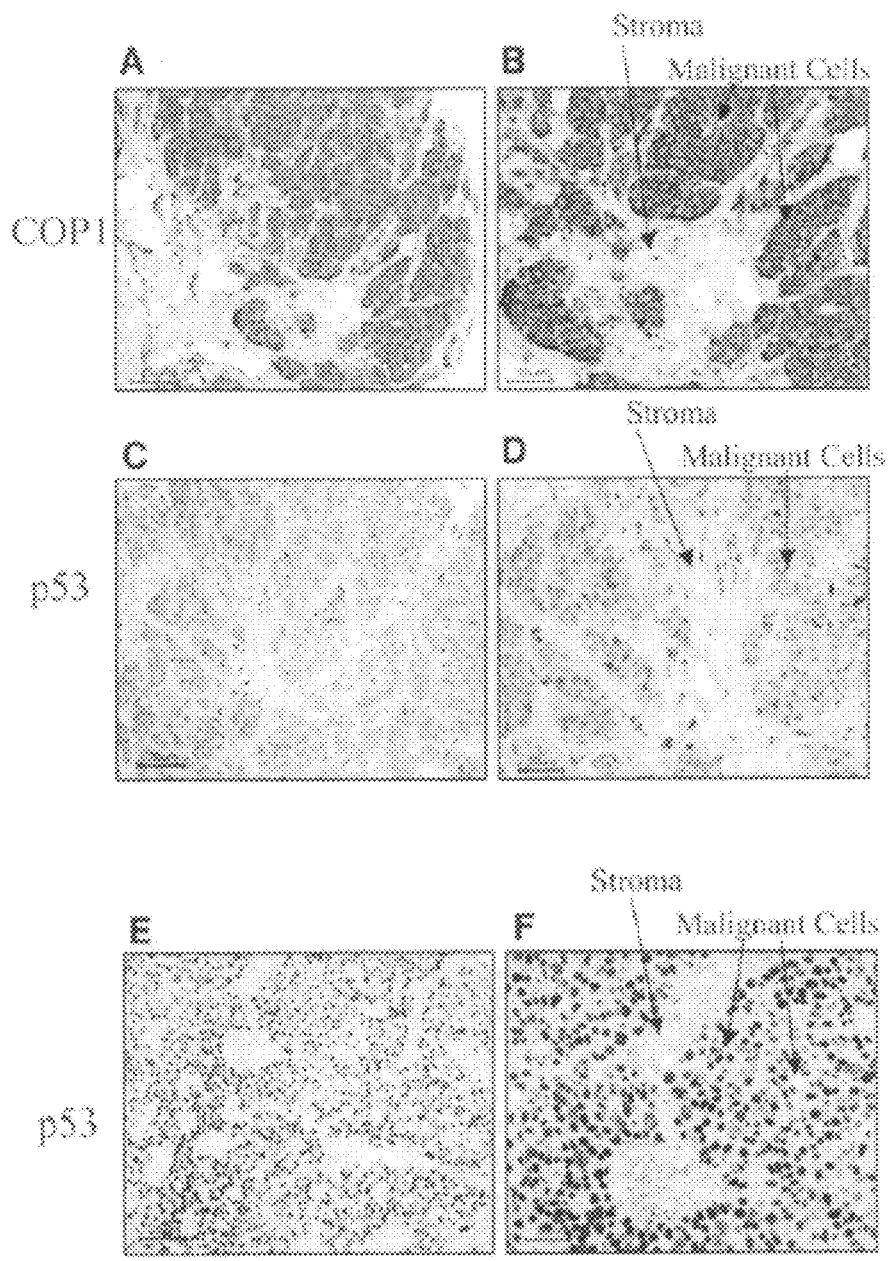
FIGS. 8A-F. COP1 overexpression in breast adeonocarcinomas. A tissue microarray that included 32 cases of breast adenocarcinomas was evaluated by immunohistochemistry for COP1 expression. COP1 immunoreactivity was identified in 25 out of the 32 breast adenocarcinoma cases. A: Representative breast adenocarcinoma showing COP1 immunoreactivity in neoplastic epithelium. B: Higher magnification of the case shown in A. C: The same breast adenocarcinoma case was negative for p53 immunoreactivity in the neoplastic epithelium although scattered stromal cells are positive. D: Higher magnification of the case shown in D. E: Positive p53 immunoreactivity in one case of breast adenocarcinoma. In total, 3/32 cases were positive for p53. F: Higher magnification of the case shown in F. The G to T transversion p53 mutation resulting in an amino acid substitution C242F, was confirmed in the IHO positive case shown in E and F. Original magnifications: ×100 (A, C, and E); ×200 (B, C, and F).

Using the COP1 specific antibody, IHC was carried out on a TMA featuring 32 cases of breast adenocarcinomas arrayed in 1 mm cores. Strikingly, 81% (25/32) of cases displayed strong immunoreactivity with the COP1 antibody (FIGS. 8A and 8B) exclusively in the malignant cells, but not within the stroma or normal epithelial cells. IHC analysis using the 1801 p53-specific antibody, which is not affected by protein phosphorylation[38], revealed only 3/32 cases with a positive signal (FIGS. 8E and 8F). In contrast, most cases that are positive for COP1 are negative for p53 FIGS. 8C and 8D). Given that p53 is difficult to detect in tissues by IHO unless stabilised by DNA damaging agents or gene mutation, the p53 gene from the breast TMA was sequenced to confirm that these particular samples were indeed mutant p53. The mutations identified in each of the three cases resulted in amino acid substitutions as follows: C242F, P278S, and R175H.

Figure 9:
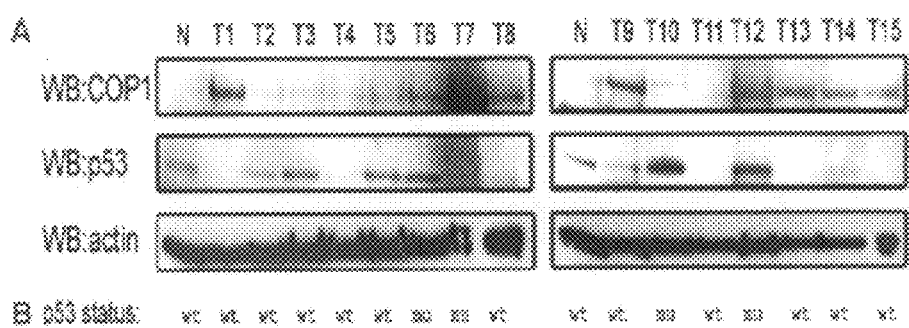
FIGS. 9A-B. COP1 and p53 steady-state levels in breast tumours. A: Lysates were harvested from normal breast or tumour samples and subject to immunoblotting with antibodies to p53, COP1, and actin. B: p53 gene status in breast tumour samples. DNA was extracted from the samples in A and subject to PCR of intron-exon boundaries and exons 5-8 of the p53 gene with the products being analysed by DNA sequencing.

To more quantitatively compare the protein levels of p53 and COP1 in breast cancer samples, we performed Western blot analysis of tumor lysates (FIGS. 9A, B). Immunoblotting with anti-COP1 revealed a very weak signal in the normal breast tissue (sample N) but a significant increase in COP1 was detected in 67% (10/15) of cases, confirming the previous observations with the breast TMA (FIGS. 8A and 8B) that COP1 is indeed overexpressed in breast adenocarcinomas. The p53 levels were reduced in 53% (8/15), but significantly increased in 20% (3/15) of the cases when compared to normal breast tissue.

To further elucidate the consequence of COP1 overexpression on p53, it was necessary to determine the p53 gene status within these samples. Therefore, exons 5-8 were sequenced and analysed for mutations at the intron-exon boundaries as well as that of the exons. 27% (4/16) of cases harboured a mutation within the exon 8 (FIG. 9B): sample T6 and T12 contained the R290H mutation, whereas samples T7 and T10 harboured the R273H mutation. The steady-state protein levels of p53 when COP1 was overexpressed in the breast tumours indicated that 75% (6/8) of the cases where wild-type p53 levels were dramatically reduced, COP1 was overexpressed. Only 25% (2/8) of cases displayed a reduction in p53 levels. Where COP1 was overexpressed and no concomitant decrease in p53 levels were observed, the p53 gene status was mutant thereby indicating that COP1 has the ability to negatively regulate wild-type p53.

The results demonstrate that at least 45% of ovarian adenocarcinomas and 80% of breast adenocarcinomas had robust overexpression of COP1, and a defect in p53 function or steady-state protein level could be seen in some samples that contained wild-type p53 and overexpressed COP1, but not in samples that contained mutant p53 and overexpressed COP1 (FIGS. 7A-D and 9A-B). Overexpression of COP1 was detected predominantly, but not exclusively, in wild-type p53 containing cancers indicating that one of the major roles of COP1 is to repress p53-dependent tumour suppression.

Examination of COP1 and p53 levels in a variety of cancers yielded the following results: for colon adenocarcinomas, 12/38 cases were p53 positive, 5 of the 12 p53 positive cases were also positive for COP1, 8 cases were COP1 positive p53 negative; for breast adenocarcinomas, 3/32 cases were positive for p53, 2 of the 3 p53 positive cases were also positive for COP1 by IHC, 23/32 cases were COP1 positive p53 negative; for transitional cell carcinoma (kidney, prostate, urinary bladder) 3/3 positive for p53 and COP1; for pulmonary adenocarcinoma 1/3 positive for p53 and COP1; for lymphoma 1/3 positive for p53 and COP1; for ovarian adenocarcinomas, 32/67 were COP1 positive, with subtype COP1 positives as follows: Serous adenocarcinoma 11/27; Endometrioid adenocarcinoma 12/19; Clear cell adenocarcinoma 4/11; Mucinous adenocarcinoma 5/10.

Thus, COP1 is overexpressed in many cancers, including breast cancers, ovarian cancers, etc. and this is concomitant with a decrease in wild-type p53 steady-state protein levels or p53-dependent transcription. We also detected COP1 by IHC in some cases of ovarian serous, endometerioid, and mucinous adenocarcinomas, where no detectable signal was observed at the mRNA level by ISH, indicating that an increase in the steady-state levels of COP1 protein can also occur at a post-translational level rather than increased transcription.

REFERENCES

The following publications are incorporated by reference herein.

1. Vogelstein B, Lane D, Levine A J: Surfing the p53 network. Nature 2000, 408:307-310
2. Hupp T R, Lane D P, Ball K L: Strategies for manipulating the p53 pathway in the treatment of human cancer. Biochem J 2000, 352 Pt 1:1-17
3. Ho J, Benchimol S: Transcriptional repression mediated by the p53 tumour suppressor. Cell Death Differ 2003, 10:404-408
4. Donehower L A, Harvey M, Slagle B L, McArthur M J, Montgomery C A, Jr., Butel J S, Bradley A: Mice deficient for p53 are developmentally normal but susceptible to spontaneous tumours. Nature 1992, 356:215-221
5. Beroud C, Soussi T: The UMD-p53 database: new mutations and analysis tools. Hum Mutat 2003, 21:176-181
6. Soussi T, Beroud C: Significance of TP53 mutations in human cancer: a critical analysis of mutations at CpG dinucleotides. Hum Mutat 2003, 21:192-200
7. Leng R P, Lin Y, Ma W, Wu H, Lemmers B, Chung S, Parant J M, Lozano G, Hakem R, Benchimol S: Pirh2, a p53-induced ubiquitin-protein ligase, promotes p53 degradation. Cell 2003, 112:779-791
8. Honda R, Tanaka H, Yasuda H: Oncoprotein MDM2 is a ubiquitin ligase E3 for tumor suppressor p53. FEBS Lett 1997, 420:25-27
9. Haupt Y, Maya R, Kazaz A, Oren M: Mdm2 promotes the rapid degradation of p53. Nature 1997, 387:296-299
10. Kubbutat M H, Jones S N, Vousden K H: Regulation of p53 stability by Mdm2. Nature 1997, 387:299-303
11. Varadan R, Assfalg M, Haririnia A, Raasi S, Pickart C, Fushman D: Solution conformation of Lys63-linked di-ubiquitin chain provides clues to functional diversity of polyubiquitin signaling. J Biol Chem 2004, 279:7055-7063
12. Juven T, Barak Y, Zauberman A, George D L, Oren M: Wild type p53 can mediate sequence-specific transactivation of an internal promoter within the mdm2 gene. Oncogene 1993, 8:3411-3416
13. Barak Y, Juven T, Haffner R, Oren M: mdm2 expression is induced by wild type p53 activity. Embo J 1993, 12:461-468
14. Neff, M. M., Fankhauser, C. & Chory, J. Light: an indicator of time and place. *Genes Dev* 14, 257-71 (2000)
15. Ma, L. et al. Light control of *Arabidopsis* development entails coordinated regulation of genome expression and cellular pathways. *Plant Cell* 13, 2589-607 (2001)
16. Ma, L. et al. Genomic evidence for COP1 as a repressor of light-regulated gene expression and development in *Arabidopsis*. *Plant Cell* 14, 2383-98 (2002)
17. Hardtke, C. S. & Deng, X. W. The cell biology of the COP/DET/FUS proteins. Regulating proteolysis in photomorphogenesis and beyond? *Plant Physiol* 124, 1548-57 (2000)
18. Seo, H. S. et al. LAF1 ubiquitination by COP1 controls photomorphogenesis and is stimulated by SPA1. *Nature* 424, 995-9 (2003)
19. Ang, L. H. et al. Molecular interaction between COP1 and HY5 defines a regulatory switch for light control of *Arabidopsis* development. *Mol Cell* 1, 213-22 (1998).
20. Yi, C., Wang, H., Wei, N. & Deng, X. W. An initial biochemical and cell biological characterization of the mammalian homologue of a central plant developmental switch, COP1. *BMC Cell Biol* 3, 30 (2002).
21. Dornan, D., Shimizu, H., Perkins, N. D. & Hupp, T. R. DNA-dependent acetylation of p53 by the transcription coactivator p300. *J Biol Chem* 278, 13431-41 (2003).
22. Dornan, D. & Hupp, T. R. Inhibition of p53-dependent transcription by BOX-I phospho-peptide mimetics that bind to p300. *EMBO Rep* 2, 139-44 (2001).
23. Frantz, G. D., Pham, T. Q., Peale, F. V., Jr. & Hillan, K. J. Detection of novel gene expression in paraffin-embedded tissues by isotopic in situ hybridization in tissue microarrays. *J Pathol* 195, 87-96 (2001)
24 Ross, S. et al. Prostate stem cell antigen as therapy target: tissue expression and in vivo efficacy of an immunoconjugate. *Cancer Res* 62, 2546-53 (2002)
25. Shimizu, H. & Hupp, T. R. Intrasteric regulation of MDM2. *Trends Biochem Sci* 28, 346-9 (2003).
26. Oren, M. Decision making by p53: life, death and cancer. *Cell Death Differ* 10, 431-42 (2003).
27. Jin, S. & Levine, A. J. The p53 functional circuit. *J Cell Sci* 114, 4139-40 (2001).
28. Schuijer, M. & Berns, E. M. TP53 and ovarian cancer. *Hum Mutat* 21, 285-91 (2003).
29. Seo, H. S. et al. LAF1 ubiquitination by COP1 controls photomorphogenesis and is stimulated by SPA1. *Nature* 424, 995-9 (2003)
30. Bianchi, E. et al. Characterization of human constitutive photomorphogenesis protein 1, a RING finger ubiquitin ligase that interacts with Jun transcription factors and modulates their transcriptional activity. *J Biol Chem* 278, 19682-90 (2003)
31. Allan, L. A. & Fried, M. p53-dependent apoptosis or growth arrest induced by different forms of radiation in U20S cells: p21WAF1/CIP1 repression in UV induced apoptosis. Oncogene. 23; 18(39):5403-12 1999
32. Qian, H., Wang, T., Naumovski, L., Lopez, C. D. & Brachmann, R. K. Groups of p53 target genes involved in specific p53 downstream effects cluster into different classes of DNA binding sites. *Oncogene* 21, 7901-11 (2002).
33. Wertz, I. E. et al. Human De-etiolated-1 regulates c-Jun by assembling a CUL4A ubiquitin ligase. Science 303, 1371-1374 (2004)
35. Shimizu, H. et al. The conformationally flexible S9-S10 linker region in the core domain of p53 contains a novel MDM2 binding site whose mutation increases ubiquitination of p53 in vivo. J. Biol. Chem. 277, 28446-28458 (2002).
36. Bianchi E, Denti S, Catena R, Rossetti G, Polo S, Gasparian S, Putignano S, Rogge L, Pardi R: Characterization of human constitutive photomorphogenesis protein 1, a RING finger ubiquitin ligase that interacts with Jun transcription factors and modulates their transcriptional activity. J Biol Chem 2003, 278:19682-19690
37. Cao Y, Gao Q, Wazer D E, Band V: Abrogation of wild-type p53-mediated transactivation is insufficient for mutant p53-induced immortalization of normal human mammary epithelial cells. Cancer Res 1997, 57:5584-5589
38. Craig A L, Burch L, Vojtesek B, Mikutowska J, Thompson A, Hupp T R: Novel phosphorylation sites of human tumour suppressor protein p53 at Ser20 and Thr18 that disrupt the binding of mdm2 (mouse double minute 2) protein are modified in human cancers. Biochem J 1999, 342 (Pt 1): 133-141
39. Wang H, Kang D, Deng X-W, and Wei, N: Evidence for functional conservation of a mammalian homologue of the light-responsive plant protein COP1. Current Biology 9:711-714, 1999.
40. Xu, H and Raafat El-Gewly, p53 responsive genes and the potential for cancer diagnostics and therapeutics development, Biotechnology Annual Review 7:131-164, 2001.
41. Soussi T, Dehouche K, and Beroud C, p53 Website and analysis of p53 gene mutations in human cancer: forging a link between epidemiology and carcinogenesis, Human Mutation 15: 105-113, 2000
42. Kmet L, Cook L S, and Magliocco A M, A review of p53 expression and mutation in human benign, low malignant potential, and invasive epithelial ovarian tumors, Cancer 97:389-404, 2003.
43. Weinberg R, Tumor suppressor gene, Science 254:1138-1145, 1991
44. Swinney D C et al., A small molecule ubiquitination inhibitor blocks NF-kB dependent cytokine expression in cells and rats, J. Biol. Chem. 277: 23573-23581, 2002.

OTHER EMBODIMENTS

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Accession numbers, as used herein, refer to Accession numbers from multiple databases, including GenBank, the European Molecular Biology Laboratory (EMBL), the DNA Database of Japan (DDBJ), or the Genome Sequence Data Base (GSDB), for nucleotide sequences, and including the Protein Information Resource (PIR), SWISSPROT, Protein Research Foundation (PRF), and Protein Data Bank (PDB) (sequences from solved structures), as well as from translations from annotated coding regions from nucleotide sequences in GenBank, EMBL, DDBJ, or RefSeq, for polypeptide sequences. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed is:

1. A method for diagnosing a cancer in a subject, the method comprising: detecting a COP1 molecule in a sample of the cancer from the subject, wherein the overexpression of said COP1 molecule relative to a control is indicative of a cancer.

2. The method of claim 1 further comprising detecting a p53 molecule in said sample, wherein a reduction in p53 expression levels or an inhibition of a p53 activity is indicative of a cancer.

3. The method of claim 2 wherein said p53 molecule is wild type.

4. The method of claim 2 or 3 wherein said p53 molecule is a human p53 molecule.

5. The method of claim 2 or 3 wherein said p53 molecule is a p53 polypeptide.

6. The method of claim 5 wherein said p53 polypeptide is detected using an antibody that specifically binds said p53 polypeptide.

7. The method of claim 5 wherein said p53 polypeptide is detected using immunohistochemistry.

8. The method of claim 2 or 3 wherein said p53 activity is selected from the group consisting of at least one of inhibition of p53-dependent transactivation, inhibition of p53-induced apoptosis, and reduction of p21 mRNA levels.

9. The method of any one of claims 1, 2, and 3 wherein said COP1 molecule is human COP1.

10. The method of any one of claims 1, 2, and 3 wherein said COP1 molecule is a COP1 polypeptide.

11. The method of claim 10 wherein said COP1 polypeptide is detected using an antibody that specifically binds said COP1 polypeptide.

12. The method of claim 11 wherein said COP1 polypeptide is detected using immunohistochemistry.

13. The method of any one of claims 1, 2, and 3 wherein said COP1 molecule is a COP1 mRNA.

14. The method of claim 13 wherein said COP1 mRNA is detected using in situ hybridization.

15. The method of any one of claims 1, 2, and 3 further comprising detecting a p21 molecule in said sample, wherein a decrease in p21 expression levels is indicative of a cancer.

16. The method of any one of claims 1, 2, and 3 wherein the subject is a human.

17. The method of any one of claims 1, 2, and 3 wherein the cancer is a wild type p53-expressing cancer.

18. The method of any one of claims 1, 2, and 3 wherein the cancer is selected from the group consisting of at least one of breast cancer, ovarian cancer, colon cancer, lung cancer, and transitional cell cancer.

19. The method of claim 18 wherein said ovarian cancer is selected from at least one of a group consisting of serous adenocarcinoma, endometrioid adenocarcinoma, clear cell adenocarcinoma, and mucinous adenocarcinoma.

* * * * *

```
                        SEQUENCE LISTING

<160> NUMBER OF SEQ ID NOS: 33

<210> SEQ ID NO 1
<211> LENGTH: 393
<212> TYPE: PRT
<213> ORGANISM: Homo sapiens

<400> SEQUENCE: 1

Met Glu Glu Pro Gln Ser Asp Pro Ser Val Glu Pro Pro Leu Ser Gln
 1               5                  10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300
```

```
Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390
```

```
<210> SEQ ID NO 2
<211> LENGTH: 21
<212> TYPE: RNA
<213> ORGANISM: Artificial Sequence
<220> FEATURE:
<223> OTHER INFORMATION: siRNA1 for COP1

<400> SEQUENCE: 2
aacugaccaa gauaaccuug a                                          21

<210> SEQ ID NO 3
<211> LENGTH: 21
<212> TYPE: RNA
<213> ORGANISM: Artificial Sequence
<220> FEATURE:
<223> OTHER INFORMATION: Inverted siRNA1 for COP1

<400> SEQUENCE: 3
aaaguuccaa uagaaccagu c                                          21

<210> SEQ ID NO 4
<211> LENGTH: 21
<212> TYPE: RNA
<213> ORGANISM: Artificial Sequence
<220> FEATURE:
<223> OTHER INFORMATION: si RNA2 for COP1

<400> SEQUENCE: 4
aagacuugga gcaguguuac u                                          21

<210> SEQ ID NO 5
<211> LENGTH: 21
<212> TYPE: RNA
<213> ORGANISM: Artificial Sequence
<220> FEATURE:
<223> OTHER INFORMATION: siRNA3 for COP1

<400> SEQUENCE: 5
aagagguguu ggaguguuga c                                          21

<210> SEQ ID NO 6
<211> LENGTH: 18
<212> TYPE: DNA
<213> ORGANISM: Artificial Sequence
<220> FEATURE:
<223> OTHER INFORMATION: Pirh2 siRNA1

<400> SEQUENCE: 6
aactgtggaa tttgtagg                                              18
```

```
<210> SEQ ID NO 7
<211> LENGTH: 20
<212> TYPE: RNA
<213> ORGANISM: Artificial Sequence
<220> FEATURE:
<223> OTHER INFORMATION: Inverted siRNA for Pirh2 B

<400> SEQUENCE: 7
aaggauguuu aaggugucaa                                                    20

<210> SEQ ID NO 8
<211> LENGTH: 21
<212> TYPE: RNA
<213> ORGANISM: Artificial Sequence
<220> FEATURE:
<223> OTHER INFORMATION: siRNA2 for Pirh2

<400> SEQUENCE: 8
aauguaacuu augccuagcu a                                                  21

<210> SEQ ID NO 9
<211> LENGTH: 21
<212> TYPE: RNA
<213> ORGANISM: Artificial Sequence
<220> FEATURE:
<223> OTHER INFORMATION: Inverted siRNA2 for Pirh2

<400> SEQUENCE: 9
aaaucgaucc guauucaaug u                                                  21

<210> SEQ ID NO 10
<211> LENGTH: 21
<212> TYPE: RNA
<213> ORGANISM: Artificial Sequence
<220> FEATURE:
<223> OTHER INFORMATION: Primer

<400> SEQUENCE: 10
aaggaauuua gacaaccuga a                                                  21

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
caggaaacag ctatgaccag ccctgtcgtc tgtcca                                  36

<210> SEQ ID NO 12
<211> LENGTH: 36
<212> TYPE: DNA
<213> ORGANISM: Artificial Sequence
<220> FEATURE:
<223> OTHER INFORMATION: Primer

<400> SEQUENCE: 12
tgtaaaacga cggccagttt caactctgtc tccttc                                  36

<210> SEQ ID NO 13
<211> LENGTH: 38
<212> TYPE: DNA
<213> ORGANISM: Artificial Sequence
<220> FEATURE:
<223> OTHER INFORMATION: Primer
```

```
<400> SEQUENCE: 13
caggaaacag ctatgacctt aacccctcct cccagaga                              38

<210> SEQ ID NO 14
<211> LENGTH: 38
<212> TYPE: DNA
<213> ORGANISM: Artificial Sequence
<220> FEATURE:
<223> OTHER INFORMATION: Primer

<400> SEQUENCE: 14
tgtaaaacga cggccagtgc ctctgattcc tcactgat                              38

<210> SEQ ID NO 15
<211> LENGTH: 38
<212> TYPE: DNA
<213> ORGANISM: Artificial Sequence
<220> FEATURE:
<223> OTHER INFORMATION: Primer

<400> SEQUENCE: 15
caggaaacag ctatgacctg tgcagggtgg caagtggc                              38

<210> SEQ ID NO 16
<211> LENGTH: 38
<212> TYPE: DNA
<213> ORGANISM: Artificial Sequence
<220> FEATURE:
<223> OTHER INFORMATION: Primer

<400> SEQUENCE: 16
tgtaaaacga cggccagtag gcgcactggc ctcatctt                              38

<210> SEQ ID NO 17
<211> LENGTH: 38
<212> TYPE: DNA
<213> ORGANISM: Artificial Sequence
<220> FEATURE:
<223> OTHER INFORMATION: Primer

<400> SEQUENCE: 17
caggaaacag ctatgaccag gcataactgc acccttgg                              38

<210> SEQ ID NO 18
<211> LENGTH: 39
<212> TYPE: DNA
<213> ORGANISM: Artificial Sequence
<220> FEATURE:
<223> OTHER INFORMATION: Primer

<400> SEQUENCE: 18
tgtaaaacga cggccagtcc ttactgcctc ttgcttctc                             39

<210> SEQ ID NO 19
<211> LENGTH: 26
<212> TYPE: DNA
<213> ORGANISM: Artificial Sequence
<220> FEATURE:
<223> OTHER INFORMATION: Primer

<400> SEQUENCE: 19
tcctctaaat gtgaattttg atgtaa                                           26
```

```
<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
tcccaactac ttttatggaa tacct                                              25

<210> SEQ ID NO 21
<211> LENGTH: 34
<212> TYPE: DNA
<213> ORGANISM: Artificial Sequence
<220> FEATURE:
<223> OTHER INFORMATION: Primer

<400> SEQUENCE: 21
ttttccaaag ttttctatgt ttggctcaat tagg                                    34

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
gtgcttagtg tacttggagt attgg                                              25

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
agtccaggcc agtatgttac ag                                                 22

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
tctgacccca aacaccttcc agc                                                23

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
aaaactggaa cggtgaaggt                                                    20

<210> SEQ ID NO 26
<211> LENGTH: 18
<212> TYPE: DNA
<213> ORGANISM: Artificial Sequence
<220> FEATURE:
<223> OTHER INFORMATION: Primer
```

```
<400> SEQUENCE: 26
cggccacatt gtgaactt                                                    18

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
atgctcgctc caaccgactg c                                                21

<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
cctttgggac attgggaat                                                   19

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
ccaccaagag cagcaatgt                                                   19

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
cccagccaac tctccaccat caa                                              23

<210> SEQ ID NO 31
<211> LENGTH: 19
<212> TYPE: DNA
<213> ORGANISM: Artificial Sequence
<220> FEATURE:
<223> OTHER INFORMATION: Primer

<400> SEQUENCE: 31
agcggattct catggaaca                                                   19

<210> SEQ ID NO 32
<211> LENGTH: 18
<212> TYPE: DNA
<213> ORGANISM: Artificial Sequence
<220> FEATURE:
<223> OTHER INFORMATION: Primer

<400> SEQUENCE: 32
ctggtcagcc aggagctt                                                    18
```

```
<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
tccacaagct gaaggcagac aagg                                              24
```